US006800459B2

(12) United States Patent
Boyes et al.

(10) Patent No.: US 6,800,459 B2
(45) **Date of Patent: *Oct. 5, 2004**

(54) METHODS AND COMPOSITIONS FOR THE MODULATION OF CHORISMATE SYNTHASE AND CHORISMATE MUTASE EXPRESSION OR ACTIVITY IN PLANTS

(75) Inventors: Douglas C. Boyes, Chapel Hill, NC (US); Keith R. Davis, Durham, NC (US); Jeffrey P. Woessner, Hillsborough, NC (US); Jörn Görlach, Durham, NC (US); Carol M. Hamilton, Morrisville, NC (US); Neil E. Hoffman, Chapel Hill, NC (US); Andreas S. Klöti, Durham, NC (US); Adel Zayed, Durham, NC (US); Robert A. Ascenzi, Cary, NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/267,763

(22) Filed: Oct. 9, 2002

(65) Prior Publication Data

US 2003/0077687 A1 Apr. 24, 2003

Related U.S. Application Data

(62) Division of application No. 09/610,040, filed on Jul. 5, 2000, now Pat. No. 6,465,217.

(51) Int. Cl.[7] .......................... C12N 21/06; C12N 9/00; C12N 1/20; C07H 21/04

(52) U.S. Cl. ...................... 435/69.2; 435/183; 435/232; 435/252.3; 435/320.1; 536/23.2

(58) Field of Search ............................... 435/69.2, 183, 435/232, 252.3, 320.1; 536/23.2

(56) References Cited

U.S. PATENT DOCUMENTS

| | | | | |
|---|---|---|---|---|
| 4,753,883 A | 6/1988 | Backman et al. | ........... | 435/232 |
| 5,120,837 A | 6/1992 | Fotheringham et al. | ..... | 536/23.2 |
| 5,187,071 A | 2/1993 | Fischer et al. | ................ | 435/32 |
| 5,776,736 A | 7/1998 | Frost et al. | ................. | 435/108 |
| 5,795,715 A | 8/1998 | Livache et al. | ................ | 435/6 |
| 5,948,612 A | 9/1999 | Bascomb et al. | .............. | 435/6 |

FOREIGN PATENT DOCUMENTS

| | | |
|---|---|---|
| WO | 96/19103 | 6/1996 |
| WO | 98/59061 | 12/1998 |
| WO | 00/05353 | 2/2000 |
| WO | 00/16609 | 3/2000 |
| WO | 00/31281 | 6/2000 |

OTHER PUBLICATIONS

Bornemann, Stephen et al., "*Escherichia coli* chorismate synthase: a deuterium kinetic–isotope effect under a single–turnover and steady–state conditions shows that a flavin intermediate forms before the C–(6proR)–H bond is cleaved", Biochem J., vol. 305, pp. 707–710 (1995).

Braun, Martin et al., Enzymatic properties of chorismate synthase isozymes of tomato (*Lycopersicon esculentum* Mill.). Planta, vol. 200 pp. 64–70 (1996).

Cotton, R.G.H. et al., "The biosynthesis of phenylalanine and tyrosine in the pea (*Pisum sativam*): Chorismate mutase". Biochimica et Biophysica Acta, vol. 156, pp. 187–189, (1968).

Eberhard, Jenny et al., "Isolation of a cDNA from tomato coding for an unregulated, cytosolic chorismate mutase", Plant Molecular Biology, vol. 31, pp. 917–922, (1996).

Gilchrist, D.G. et al., "Chorismate Mutase from Mung Bean and Sorghum", Methods in Enzymology, vol. 142, [54] pp. 450–463, 1987).

Gilchrist, D.G. et al., "Regulation of Aromatic Amino Acid Biosynthesis in Higher Plants, Properties of an Aromatic Amino Acid–Sensitive Chorismate Mutase (CM–1) from Mung Bean", Archives of Biochemistry and Biophysics, vol. 164, pp. 95–105, (1974).

Gilchrist, D. G., "Regulation of Aromatic Amino Acid Biosynthesis in Higher Plants, Properties of an Aromatics Amino Acid Insensitive Chorismate Mutase (CM–2) from Mung Bean", Archives of Biochemistry of Biophysics, vol. 171, pp. 36–42, (1975).

Gorisch, Helmut, "Chorismate Mutase from *Streptomyces aureofaciens*", Methods in Enzymology, vol. 142, [55] pp. 463–472, (1987).

Gorisch, Helmut, "A New Test for Chorismate Mutase Acitivity", Analytical Biochemistry, vol. 86, pp. 764–768, (1978).

(List continued on next page.)

*Primary Examiner*—Tekchand Saidha
(74) *Attorney, Agent, or Firm*—Laura L. Kiefer; Timothy G. Hofmeyer; Deborah H. Spencer

(57) ABSTRACT

The present inventors have discovered that chorismate mutase and chorismate synthase are essential for plant growth. Specifically, the inhibition of chorismate mutase or chorismate synthase gene expression in plant seedlings results in severe chlorosis, reduced growth and developmental abnormalities. The inventors have proven that chorismate synthase and chorismate mutase can be used as targets for the identification of herbicides. Thus, the invention provides methods for the identification of chemicals that modulate chorismate synthase and chorismate mutase biochemical reactions. The methods of the invention are useful for the identification of herbicides and for the inhibition of plant growth and development.

5 Claims, 5 Drawing Sheets

OTHER PUBLICATIONS

Henstrand, John M. et al., "Cloning and Characterization of a Heterologously Expressed Bifunctional Chorismate Synthase/Flavin Reductase from *Neurospora crassa*", The Journal of Biological Chemistry, vol. 270, No. 35, pp. 20447–20452, (1995).

Krappmann, Sven et al., The aroC Gene of *Aspergillus nidulans* Codes for a Monofunctional, Allosterically Regulated Chorismate Mutase, The Journal of Biological Chemistry, vol. 274, No. 32, pp. 22275–22282, (1999).

Kuroki, Gary W. et al., Purification and Characterization of an Inducible Aromatic Amino Acid–Sensitive Form of Chorismate Mutase from *Solanum tuberosum* L. Tubers, vol. 260, No. 2, pp. 616–621, (1988).

Macheroux, Peter et al., Studies with Flavin Analogs Provide Evidence That a Protonated Reduced FMN Is the Substrate–induced Transient Intermediate in the Reaction of *Escherichia coli* Chorismate Synthase, The Journal of Biological Chemistry, vol. 271, No. 42, pp. 25850–25858, (1996).

Ramjee, Manoj K. et al., "A Continuous, Anaerobic Spectrophotometric Assay for Chorismate Synthase Activity That Utilizes Photoreduced Flavin Mononucelotide", Analytical Biochemistry, vol. 220, pp. 137–141 (1994).

Schmidheini, Tobias, et al., "A Single Point Mutation Results in a Constitutively Activated And Feedback–Resistant Chorismate Mutase of *Saccharomyces cerevisiase*", Journal of Bacteriology, vol. 171, No. 3, pp. 1245–1253, (Mar. 1989).

Schmidheini, Tobias et al., "Yeast Allosteric Chorismate Mutase Is Locked in the Activated State by a Single Amino Acid Substitution", Biochemistry, vol. 29, No. 15, pp. 3660–3668, (1990).

Singh, Bijay K. et al., Chorismate Mutase Isoenzymes from *Sorgum bicolor*: Purification and Properties, Archives of Biochemistry and Biophysics, vol. 243, No. 2, pp. 374–384, (1985).

White, Peter J., et al., "The overexpression, purification and complete amino acid sequence of chorismate synthase from *Escherichia coli* K12 and its comparison with the enzyme from *Neurospora crassa*", Biochem J., vol. 251, pp. 313–322, (1988).

Woodin, Terry S., et al., "Evidence for Three Isozymes of Chorismate Mutase in Alfalfa", Biochimica et Biophysica Acta, vol. 309, pp. 211–223, (1973).

Dell, et al. , "Identification and removal of impediments to biocatalytic synthesis of aromatics etc.", J. Am. Chem. Soc., Am. Chem.Soc.(U.S.). vol. 115, p. 11581–11589 (1993).

Eberhard, Jenny et al., "Cloning and expression in yeast of a higher plant chorismate mutase molecular cloning, sequencing of the cDNA and characterization of the *Arabidopsis thaliana* enzyme expressed in yeast", FEBS, Elsevier Science Publ.B.V., vol. 334(2), pp. 233–236, Nov. 1993.

Bornemann, Stephen et al., "*Escherichia coli* chorismate synthase catalyzes the conversion or (6S)–6–fluoro–5–enolpyruvylshikimate–3–phospha to 6–fluorochorismate", The Journal of Biological Chemistry (U.S.), vol. 270(39), pp. 22811–22815, Sep. 29, 1995.

Mobley, Evelyn M. et al., "Identification, characterization and comparative analysis of a novel chorismate mutase gene in *Arabidopsis thaliana*", GENE, Elsevier Science B.V., vol. 240, pp. 115–123, (1999).

Andrews, P. R. et al., "Rearrangement of Chorismate to Prephenate use of Chorsimate Mutase EC—1.3.1.12 Inhibitors to Define The Transition State Structure", Biochemistry, vol. 16(22), 1977, pp. 4848–4852.

Eberhard, J. et al. "Cytosolic and Plastidic chorismate mutase isozymes from *Arabidopsis thaliana*: Molecular characterization and enzymatic Properties", Plant Journal, Blackwell Scientific Publications, Oxford, GB, vol. 10(5), 1996, pp. 815–821, XP002180796, ISSN: 0960–7412; Database Accession No. L47355, retrieved from WWW2.EBI.AC.UK.

Shaller, A. et al., "*Arabidopsis thaliana* CM2 gen for cytosolic chorismate Mutase Exon 1–6", Database EMBL 'Online! EBI; Sep. 2, 1999; retrieved from WWW2.EBI.AC.UK; Database accession No. AJ242648, XP002225852.

Shaller, A. et al., "*Arabidopsis thaliana* CM1 gene for plastidic chorismate Mutase Exons 1–6", Database EMBL 'Online! EBI; Sep. 2, 1999; retrieved from WWW2.EBI.AC.UK; Database accession No. AJ242647, XP002225853.

Azamizu, E. at al., "*Arabidopsis thaliana* cDNA clone: RZ121d05R, 5' end" Database EMBL 'Online!EBI; Jun. 16, 2000, retrieved from WWW2.EBI.AC.UK; Database accession No. AV551112, XP002225854.

Shaller, A. et al., :Molecular Cloning and Analysis of a cDNA coding for chorismate synthase from the higher plant *Corydalis sempervirens* Pers, Journal of Biological Chemistry, American Society of Biological Chemists, Baltimore, MD, US., vol. 26(32), Nov. 15, 1991, pp. 21434–21438; XP002120077; ISSN: 0021–9258.

Bass, Brenda L., "Double–Stranded RNA as s Template for gene silencing", CELL, Cell Press, Cambridge, NA, US., vol. 101(3), Apr. 28, 2000, pp. 235–238, XP002194756, ISSN:0092–8674.

Roberts, F. et al., "Evidence for the Shikimate pathway in apicomplexan parasites", Nature (London), vol. 393(6687), Jun. 25, 1998, pp. 801–805, XP0021210883, ISSN: 0028–0836.

Tang, Y. et al., "In–Vivo Catalysis of a Metabolically essential Reaction by an Antibody", Proceedings of the National Academy of Sciences of the United States, vol. 88(19), 1991, pp. 8784–8786, XP002225850, ISSN: 0027–8424.

FIG. 1

2X CaMV Constitutive promoter

Gal4 DNA binding domain

2x VP16 Activator domain

SEQUENCE LISTING

```
<160> NUMBER OF SEQ ID NOS: 11

<210> SEQ ID NO 1
<211> LENGTH: 1053
<212> TYPE: DNA
<213> ORGANISM: Arabidopsis
<220> FEATURE:
<221> NAME/KEY: misc_feature
<222> LOCATION: (1)...(1053)
<223> OTHER INFORMATION: n = A,T,C or G

<400> SEQUENCE: 1

caatcccttt gttgagttgg gaatacagtt ttgcagttct ggtcagttta tgaacaccgt      60

ttacaagccc aagtgggatt tccgacaatg caggtcaaaa cccaccaaca agatttcctt     120

atgctcttga cggattcatt cgcagttatc tctttttcgg attattcgga tttagggctt     180

ctgacaatgt tattttctat ctgtcggagt gtaaattctc gtgtctacca attcttctgg     240

aagtacacat tggtgaactt gcgagacata ggcaagattc tcagttcctg caaattgctt     300

caaaattctc ttgcccaaag ctccaggagc aactcttcca atggtctctc tagctgaaga     360

tcttcctcca ccctgcactg atctgacacc atacttcatg tcataagttg catcagcatg     420

cgatggtcta taggcaaccg acatttcact gtaatcaagt cctctctgat ctgtgtttgg     480

tacaaacaca tggataggtg ttcctgtcgt cattccttca gagactccag acgatatccg     540

gcaagtatca gtctcttttc taggagttgt gatcctgctc tgaccaggcc tccttctatc     600

gagatcgaat tgcaaatcag attcagtaag tggaatacga ggaggacaac catcaatgat     660

acaaccaact cctcctccat gtgattctcc aaaagttgaa actcgaaaat gagtcccata     720

tgaacttcca gtagcttgta tctggaagtt cttcctggtt tgggtacgga gagagatctg     780

aacggcggga gaagagagac gacggagctc cgagggaaga gaagaagaac cgagtttggt     840

ggatccgaga atggatttcg aagtgagaga agacgacgcc atgatcagga ttccaaggca     900

gaagaaagat gattgagaaa ggtttaaagg agagaaattt gaagttggtg gcaattttga     960

gcggacgcgt gggtcgaccg cgggaattcc gagacccggt acctgcatgg cgtactcagc    1020
```

-continued

```
tnncncctgg gcnngagttt tccntagaga agt                              1053


<210> SEQ ID NO 2
<211> LENGTH: 1207
<212> TYPE: DNA
<213> ORGANISM: Arabidopsis

<400> SEQUENCE: 2

gcgtcattgt tgatgagatc gtcttgttgc tcctctgcga ttggtgggtt cttcgaccat     60

cgacgtgaat tatcaacctc aacacccatt tccactcttc ttcctcttcc atcaaccaaa    120

tcttctttct ctgttcgttg ttctcttcct cagccatcaa agccacgctc tggaaccagc    180

tctgttcacg ccgttatgac actcgctgga tcgttgacag ggaagaaacg agtggatgag    240

agtgagagtt tgactcttga aggtattaga aactctttga tccgtcaaga ggacagcatt    300

atatttgggc tattggagag agccaagtac tgttacaatg ctgatactta tgatcctact    360

gcttttgaca tggatggttt caatggttct ttggttgagt acatggttaa aggcactgag    420

aagcttcacg ctaaggttgg taggtttaag agtcctgatg aacatccttt cttccctgat    480

gatctaccag agcctatgtt gcctcctctt cagtacccaa aggtgttgca ttttgctgct    540

gattcgataa acataaacaa gaagatatgg aacatgtact tcagagacct tgttccaaga    600

cttgtgaaga aaggcgatga tggtaactac ggctcaacag ctgtctgtga cgctatctgc    660

cttcagtgtc tctcaaagag aatccattac ggtaaatttg ttgcagaagc taaatttcaa    720

gcctcacccg aagcatacga gtccgccatc aaagcacaag ataaggatcg actgatggat    780

atgctgacat tcccgactgt ggaagatgcg ataaagaaga gagttgagat gaaaacccga    840

acatacgggc aagaagtgaa agttgggatg gaggagaaag aagaagaaga agaagaaggg    900

aatgaatctc atgtttacaa aatcagtccg atcttagttg gtgacttata tggagattgg    960

atcatgcctt taacaaaaga ggttcaagtg gagtacttgc tcagaagact ggactgaggc   1020

aacaacaaaa taaacaatat ggctttggta gtagagtaga aaggtttttg aatgttcttt   1080

ggtttttttt ttttacttta caatatttct aaacgttgtt acactattat tccactgtac   1140

aaagcgtgca tggtcagtgg tattgaagaa gggtaattag ccgttactca aacggtgtcg   1200

tttatgt                                                            1207


<210> SEQ ID NO 3
<211> LENGTH: 1006
<212> TYPE: DNA
<213> ORGANISM: Arabidopsis

<400> SEQUENCE: 3

ctttagcatt gaggaagaag aagaagaaag cttcattttt ccaggggata cagttgaagc     60

ggcatggcaa gagtcttcga atcggattcg ggttctggtt gttccaatgt actgagtctt    120

gacttaatca gagaatcgtt gattaggcaa gaagacacca tcgtcttcag cttgatcgag    180

agagctaagt ttccactcaa ttctcctgct ttcgaggaat ctcgttgtct agattctgga    240

agtttctctt ctctcactga gtttttcgtc agagagacag aaatcatcca agctaaggta    300

ggaagatatg aatacccgga agagaatcct ttcttccttg agaacattcc tcactcggtt    360

tttcctacgc acaaatatcc atcggctttg caccctaagg ctctatctgt taacattaac    420

aaacaaatct gggatattta ctttaaagaa ttgcttcctt tgtttgtcaa acctggcgat    480

gatggcaact atccatcaac tgctgctagt gatctcgcct gtttacaagc tctttcgaga    540

aggattcact acggtaaatt tgtagctgag gtcaaattca gagatgctcc acaagattac    600
```

-continued

```
gagcctgcga ttcgcgctca ggatagagag gctttgatga agctgttgac gtttgagaaa    660

gtagaagaaa tggttaagaa gagagtgcag aagaaagcag aaacgtttgg acaagaagta    720

aaattcaact ctggctatgg cgatgagagt aagaagaagt ataaagtgga tccattgctt    780

gcctctcgca tctacgggga atggcttatc cctctcacta agctcgttga ggttgagtat    840

cttctacgtc gtctcgattg aatattattt gtatccaaat ctggccctgt taaagtgggc    900

cttaagtttt taagtgggcc tgttgatatt tgtcaggata tgatagaata attgaatgaa    960

gcaacacagt catcactatt ttaaattttg taagatattt taagga                  1006
```

<210> SEQ ID NO 4
<211> LENGTH: 1217
<212> TYPE: DNA
<213> ORGANISM: Arabidopsis

<400> SEQUENCE: 4

```
tctcgaccag ataattttgt aacggattgg atttttttgt gtcactatcc gatttttatt     60

tttcctaact ccgccgaatc cgttcctctg tccttttctt tctccactct ctgtctctgt    120

ctcttcctct tttgattctc cgatggaggc taagttactc aaacccgcgt tttacaattc    180

cccaaacctc aatcttacga attcttcaag actcatctcg cgattatcaa tctggaacga    240

taaatcaaaa gttggactat cttctgggtc tctcttcctc cgtctctccg cagcttctcc    300

gatccgatac tctagggggc tactaagggt agatgagagt gagtatttga aacttgaaag    360

cattagacac tctttgattc gtcaagagga cagtattatc tttaatcttc ttgaacgagc    420

tcagtatcgc tacaacgctg atacttatga cgaggatgcc tttactatgg aagggtttca    480

aggatcttta gttgagttta tggtcagaga aactgaaaag cttcacgcaa aggtggacag    540

gtacaagagt cctgatgagc atcccttttt cccacaatgc ttgcctgaac ctatccttcc    600

tcctattcaa tacccacagg ttttgcatcg ttgcgccgaa tcgataaaca tcaacaagaa    660

ggtgtggaat atgtatttca aacaccttct ccccagactg gtcaagccag gggatgacgg    720

taattgtggt tcagctgctc tctgtgacac aatgtgtttg cagatacttt caaagagaat    780

tcacttgcgt aaatttgttg ctgacgccaa gtttcgtgaa aatcctgctg cctatgaaac    840

agctatcaaa gaacaagacc ggacacagct gatgcaactt ctaacgtacg aaacggttga    900

agaagtagtc aagaagagag ttgagatcaa agccagaatt tttggtcaag acataacgat    960

taacgaccca gaaactgaag ctgatccttc ctacaaaata caacctagct tagttgcaaa   1020

actctatgga gaaaggatca tgcccctcac aaaggaagtc caaattgagt acttgcttag   1080

aagactggat taatgttttc aaagaaggaa gcataacatt tgtattgatc ctatttttcc   1140

gaaaaccata atgttgacat aagctgcgca agctagcaag tcaagttgat tttattaaaa   1200

aaccctgacg tagctcg                                                  1217
```

<210> SEQ ID NO 5
<211> LENGTH: 5099
<212> TYPE: DNA
<213> ORGANISM: Arabidopsis thaliana
<220> FEATURE:
<221> NAME/KEY: misc_feature
<222> LOCATION: (1)...(5099)
<223> OTHER INFORMATION: n = A,T,C or G

<400> SEQUENCE: 5

```
ggatccgctc aactcttttg atccttgagg atgatcacga ccgaatgctt tgaggagaag     60
```

-continued

```
agtggtttat ttttgttgta ttgacaaaaa cttctacaat aactttgttt tgctttgaca    120
tttctcacaa tttttatctg tctagattcc aaaagcgatt tttaagtgtc cttgcaccca    180
ctcaaattct gatgattttc tatccaccta atgtggattt cactttaatt ctctttttct    240
aattaaaata agctactgta ttttttttcc ttagcttgag gacattttta aagtttttta    300
ttttgaaatc gtcactttct aaaatatatg atttgtagtt tcaactaaaa gcggatgaca    360
aaagaaaatt gtagttattt tcccaatttt tttgaatcca tagttagtta attatttggg    420
taatattaca aagtagtcaa aatttgaatc aaaataaagt aattaactat tgtcagtttt    480
ttatcggtaa atgaacatat gacgtcacaa taaaagacaa aaatatccca acaagtcgaa    540
ccaaaaacaa acacttgcgg aaaaaaaaac atagatatga aagattttaa caaaagtaac    600
attttataac gaactttttg aaaattagca tgttatatta aaaataccat ttcactttaa    660
aaaaagtaca atgtgaaata aaataataac atgatatgta ttataatagc gtgtcaaata    720
aaaaacaaag ctgattaata ttaaaaagta acatgaaatc ttaagaaact attcattttc    780
aaccgtcaat tagtattgta attaaaaagt gtgtaagact caaagaatac tattggatca    840
aatggttatg ggcttcgttt acgagagaga cgcgatgggt tgagtccttt gttttagcaa    900
agaaaatttt ttagaaattt ctaaaaatag cactaaaaca agttttatgg acaataatag    960
cacacactcc atagacttct aaaaatagca ttatttgact tactatgaag tttttgttct   1020
aaaagtatta tcactaattt attttttcaa taataccaca atatttatat aaaacctatt   1080
caaccaaaat aaattagaaa taaatttaaa atattatatt tgggttctgt atttccaatt   1140
tatggtatat atttcaacca tttaaaagaa attttgatca ttttaatatt actttatggt   1200
attatatttg ggttccctct ttccaattta tgatatatat tttcactgtt taaaagagat   1260
ttttcatttt aatattagtt tgtggtatta tatttgggtt ctctatttcc aatttagggt   1320
atatatttcc actatttaaa aaaaatgtga ttcaatttaa tattagtgtt tgctctcatt   1380
tttatttggg agattgacac aaatgacact taaaaacttt attatttaat taatttctaa   1440
agaattaaaa actttatgtg ctatttttgg aagtttaaaa aaaaagtgtt atttttggaa   1500
taataaagtt tttaatgtca tttgtgtcaa ttccacaaaa attaaaaact tttataccaa   1560
catacaaacg aagtcatttt gagtagacac ctcatcatgc atgtgttagc tgactcaaca   1620
acctattaat tacacaaaat ttcaaatcga aaactatact atacagattg tatgagcata   1680
aaaatattaa ttcaagacga agtcattaaa atatcgaaaa ctatactata cagattgtat   1740
gagcataaaa atattatatt ttcatcacaa aagaatcatc tacagtaaaa acgtatatat   1800
aatagttttt ataatcatat atatgaaagt tggccaactc tctccatatg attgatacat   1860
catcacttta acatttgata tatcatcact ttaacattta ccatgtgtcc actgaataat   1920
taatgtaagc tcttcaactt ttaattttta gattaatgat gtatttatta tttaatttta   1980
ctaatacata atttattttg ttattacatg ttcttcaata aaattatttt attggttttc   2040
tcatactcga agaatttttt ctgtaatctt aactcaaatt atgagtgtat agtagttatg   2100
gattagttaa taatttgaat agtttgcata ttgttatata tctatatagt aaatcgccga   2160
gggtgaagag tatgtaagaa gtttaatcat caaattctta ggtttcgaga atctcaatat   2220
taccttctat ttaattagtt taagacgaac attgtttagg aattgtgtgt ataatgcatt   2280
gttgaaaatg ttgttaggaa aaaatatttt aatactaaaa ataattactt attacataag   2340
taaatgatta gataattaaa aattatattt aaattaaacg atacaaaaaa tctaaaaata   2400
ctgcagcgta acgtgggtaa ttacctagtt tgtaataaat aataattcaa gacgttagaa   2460
```

-continued

```
aaagagagga taattcactg ctcttctata cactatttgt tcatatttaa attctttatt   2520
cttttcatat cattggtagt ttatatatat attatgtagt tatttaatcc ttgtttgatt   2580
gtttctatgt atcgaccaaa aaaatataca aagttgaatc ttaaaatatt gttttcatat   2640
taatattcta aactttggta aagttgtaag ttataaaaca acttgaacat aaaaataatg   2700
attgaaatta atgagagaac acaaaataga aaaaaaaagg tcatgagaac agaacagaaa   2760
cacttttgtg gctttcgtgg gctaaagacg tgcacgcaga cacaacccta aacatctctc   2820
cctctctcac caactctttc tctttaccca ctgcacctac ccccaaacaa tccctttttaa  2880
catctctcat tcctctgctc atgattcttt gtctcttcct ctgatttctc aatcctctgt   2940
tttctccgtc tcctctgttt ttttcacatc aatggaagcg tcattgttga tgagatcgtc   3000
ttgttgctcc tctgcgattg gtgggttctt cgaccatcga cgtgaattat caacctcaac   3060
acccatttcc actcttcttc ctcttccatc aaccaaatct tctttctctg ttcgttgttc   3120
tcttcctcag ccatcaaagc cacgctctgg aaccagctct gttcacgccg ttatgacact   3180
cgctgggtac gaaagtctca atctttagat tctaattgag aaattgagat taccctttttt  3240
gttacctttc atgatttgta gattcccatt gtgaaattaa cataaccctt tgtgattttg   3300
tagcttaaat tagaaacctt tatgttcttc ttagatgaat ttgaagcaaa gttttgtttt   3360
tgtttgttgt tgttgttgat atagatcgtt gacagggaag aaacgagtgg atgagagtga   3420
gagtttgact cttgaaggta ttagaaactc tttgatccgt caagaggaca gcattatatt   3480
tgggctattg gagagagcca agtactgtta caatgctgat acttatgatc ctactgcttt   3540
tgacatggat ggtttcaatg gttctttggt tgagtacatg gttaaaggca ctgagaagct   3600
tcacgctaag gtaacaaaca catgctcttt attaacatac cctcaagatt gaaacttgac   3660
tttgttatgg aacttgatta ggttggtagg tttaagagtc ctgatgaaca tcctttcttc   3720
cctgatgatc taccagagcc tatgttgcct cctcttcagt acccaaaggt actcaatata   3780
catgtttcac atgaaaaaag atcgtctcct ttatgttttc ttgcatctta ccgatatggt   3840
ttcttgatgt tcggtgaagc aatgtgtaat cttgtttgag atgtgttttc aacttctgta   3900
ctttggtgct gaggattcaa gtttctttct tattgtatag gtgttgcatt ttgctgctga   3960
ttcgataaac ataaacaaga agatatggaa catgtacttc agagaccttg ttccaagact   4020
tgtgaagaaa ggcgatgatg gtaactacng ctcaacagct gtctgtgacg ctatctgcct   4080
tcaggtttgt tcctttttttt ccttttgtta ggtatcagaa acaagcttgg atatttgttt  4140
aaaaacttgt cacctctttt ctaagtcgat taacgtctca tgtagttttt gatgtccatt   4200
gcagtgtctc tcaaagagaa tccattacgg taaatttgtt gcagaagcta aatttcaagc   4260
ctcacccgaa gcatacgagt ccgccatcaa agcacaagta tttatctact tctctaaagc   4320
tctcacatac acacaaaaac tcgaagttta tgcattactt accttttgac atggcaacat   4380
acgcattgca ggataaggat gcactgatgg atatgctgac attcccgact gtggaagatg   4440
cgataaagaa gagagttgag atgaaaaccc gaacatacgg gcaagaagtg aaagttggga   4500
tggaggagaa agaagaagaa gaagaagaag ggaatgaatc tcatgtttac aaaatcagtc   4560
cgatcttagt tggtgactta tatggagatt ggatcatgcc tttaacaaaa gaggttcaag   4620
tggagtactt gctcagaaga ctggactaag gcaacaacaa aataaacaat atggctttgg   4680
tagtagagta gaaaggtttt tgaatgttct ttggtttttt ttttttactt tacaatattt   4740
ctaaacgttg ttacactatt attccactgt acaaagcgtg catggtcagt ggtattgaag   4800
```

-continued

```
aagggtaatt agccgttact caaacggtgt cgtttatgta catactctca attgtggaaa   4860
cctgtatatg agttttagtc gctcttattt gttttggaga tgtatttttt tgtgtgttag   4920
tgcctgtaga atgataattg gctgcttagt gtagtggtca ccactggtta tatggagttt   4980
gactcgtctc atatggagtc cgactccatc cattgtaaaa gtggaaatgg gtcactagga   5040
gagagccttc tcgtcatcct cctgtgttaa cttacaagga aagagccttc tagtcatcc    5099
```

<210> SEQ ID NO 6
<211> LENGTH: 5176
<212> TYPE: DNA
<213> ORGANISM: Arabidopsis thaliana

<400> SEQUENCE: 6

```
tctttgggac cactgtcggc agaggcatct tcaacgatgg cctttccttt atcgcaatga     60
tggcatttgt aggagccacc ttccttttcc actatcttca caataaagtg acagatagct    120
gggcaatgga atccgaggag gtttccggat attacccttt gttgaaaagt ctcaattgcc    180
ctttggtctt ctgagactgt atctttgata tttttggagt agacaagtgt gtcgtgctcc    240
accatgttga cgaagatttt cttcttgtca ttgagtcgta agagactctg tatgaactgt    300
tcgccagtct ttacggcgag ttctgttagg tcctctattt gaatctttga ctccatggcc    360
tttgattcag tgggaactac ctttttagag actccaatct ctattacttg ccttggtttg    420
tgaagcaagc cttgaatcgt ccatactgga atagtacttc tgatcttgag aaatatatct    480
ttctctgtgt tcttgatgca gttagtcctg aatcttttga ctgcatcttt aaccttcttg    540
ggaaggtatt tgatttcctg gagattattg ctcgggtaga tcgtcttgat gagacctgct    600
gcgtaagcct ctctaaccat ctgtgggtta gcattctttc tgaaattgaa aaggctaatc    660
tggggacctg caggcatgca agcttcttgg tggaaagaca ctgcttatat agtctctgaa    720
cgtattccag aaccttctag aatcactcac agctctcgaa ctcatcctta ccctctctca    780
aggtgagaat ttggtgtttc atatttcatt acaaaatgta aaaaacagag tatgtaactt    840
ttgtgaaaat gcaacatgtt tattaatgga ttttctcaat tcattccaat gtaataagta    900
gagagatatg agtaccaatt tggtcatgac atcataaaag catagagctt agtaacttct    960
tccccagtag ctccacttct tgggtggctt tcctgatgca aagcatagag tctcttctcc   1020
tagttcaggc tgctcaagag gagtacatag agtcttagct cctcctcctc ctcctcctgt   1080
ttcatcacct ctggtacgcc tcttcacatc cttctccact tcaaccttat cacaccatgg   1140
agctaaaatc agtttctttt ggctcaaagc ttccacaaat tcatcccaag tttcaacctt   1200
ttgagtacat tcttcaacct ttctctttgc cacatcatag aggttactct ggattttctc   1260
tagcaagtcc ttaacttgtt caatcaaatc ccctctcttg acatccatct tagctccatt   1320
gtcacgcgtc actatcctcc ctgatcattg gccaaatctc taggtccagt ttcaattctc   1380
aaaggaacac cgttagttct tgatccgcat acttccatcc gcaagaatag ttgtcgcgta   1440
tatctgcttc agcacggatt ccagccccaa gcaaggtgga ttcaacagct tcacaagcat   1500
cacaaagttc ttgataatca gcagcgcctt tgatgggaac atggattaca acaacttgaa   1560
caggtgccac tttaggaggg aatactaaac ctttgtcatc tccatgagtc atacacgcgg   1620
ctgtagatgt tcaaacatca agcacctcct catcagcctc ttctttggta gcaaaatcag   1680
tgtgtccttc ttgccaaagg aactcacggc tcctgataaa tggggtaggg tcgctaaact   1740
cccatctaac aacgtaacat tagcccactg gttaaccttc aaagggaggt ccctgtgtcc   1800
tcttatccac cagctcttgt aacccaagca acctctggag caaacccttg agtgtggtct   1860
```

-continued

```
ttctccttct caagagaatc acgtgttaca aacatcggga aatagtattc atccactttc   1920
atcttctcaa tctcagcgtt gaagaacgtt cgtataacgt tccaaatatt catcgctgat   1980
gcctgatggc ttgagaatgt agcatccctt tacagactcg tagtattcaa ccaattcacc   2040
aaatctacaa gcctcggaat accacttccc aaaatcttca tctttctttg cagtgattcc   2100
aagacgagtt tctttcacca tctctttcac tttcctagag gcttctcgag gaattgcttg   2160
acttgtcaca caaccttaga gcgtaagcca gaaaaataat tcagaacaat acaaataaac   2220
cccagctatt gtgagaagat ataataattc tttatgggcc agtcggtgaa tatagttggg   2280
cccaaatcat cggatgtgga tcttgttttg atttcaacgc tttcgttttt ttttgtttct   2340
gttttccttg attgaggaag caatctatgc aaagaggtcc aaaacacttt agcattgagg   2400
aagaagaaga agaaagcttc atttttccag gtaataagtc ctttgacttt cgtcattcac   2460
aattgctcat ctctatagtt tctatgaatg aattgtttgc ttacttatac accatcaagc   2520
aggggataca gttgaagcgg catggcaaga gtcttcgaat cggattcggg ttctggttgt   2580
tccaatgtac tgagtcttga cttaatcaga gaatcgttga ttaggcaaga agacaccatc   2640
gtcttcagct tgatcgagag agctaagttt ccactcaatt ctcctgcttt cgaggaatct   2700
cgttgtctag attctggaag tttctcttct ctcactgagt tttcgtcag agagacagaa   2760
atcatccaag ctaaggtttg cttcccattt taaaaactga tccttttgct aaaattagat   2820
acagagatat caatgcttcg tttgattcgg ttttggtata gcattgtttt agattgttcc   2880
atgaaattag cagaaagtaa gctacaagtc aacttgattg aggttttaat aagcctggat   2940
tcttgaatta gcatgccttt tgtttgctat gtgtctcctc cattgcaaaa gatgataact   3000
tggctttgcc tgtataatct cattgtgtga taacttcttg ttttgatttg agtgcgaatc   3060
tgccaataaa aggctccgac tttatcatat gtatacgaga tttccttatg aaaacctcat   3120
tatatgtgga gattggaaat ggaggactat tgttttctat ttttataatg tctgaaagtc   3180
ttatttcatt aatatattca tctcattggt ttatattctt aagtttctgg atattgagcc   3240
tatatgtttg ttcattggtt tacttgaaaa ccttatgtgt atgtgtatat tatataggta   3300
ggaagatatg aatacccgga agagaatcct ttcttccttg agaacattcc tcactcggtt   3360
tttcctacgc acaaatatcc atcggtatgt atgtagtaaa gtcttgagca tttttcttag   3420
aactctgaat gctttagtct aacagtactt ttctttctct tgattaggct ttgcacccta   3480
aggctctatc tgttaacatt aacaaacaaa tctgggatat ttactttaaa gaattgcttc   3540
ctttgtttgt caaacctggc gatgatggca actatccatc aactgctgct agtgatctcg   3600
cctgtttaca agtaaggaga tgattgagta tacataacaa aatcagctct acttttggct   3660
aatgatgtct gatctgatat gtttgatctt gtgtaaggct ctttcgagaa ggattcacta   3720
cggtaaattt gtagctgagg tcaaattcag agatgctcca caagattacg agcctgcgat   3780
tcgcgctcag gtaaacttag tgtcacattg tggattctgt ttcactgtgg ttttaaaatg   3840
atatgattca caccataatc gtttgatttt cgactgtagg atagagaggc tttgatgaag   3900
ctgttgacgt ttgagaaagt agaagaaatg gttaagaaga gagtgcagaa gaaagcagaa   3960
acgtttggac aagaagtaaa attcaactct ggctatggcg atgagagtaa gaagaagtat   4020
aaagtggatc cattgcttgc ctctcgcatc tacggggaat ggcttatccc tctcactaag   4080
ctcgttgagg ttgagtatct tctacgtcgt ctcgattgaa tattatttgt atccaaatct   4140
ggccctgtta aagtgggcct taagtttata agtgggcctg ttgatatttg tcaggatatg   4200
```

-continued

```
atagaataat tgaatgaagc aacacagtca tcactatttt aaattttgta agatatttta   4260

aggaaaagaa aaaagtcgcc agtatttcgc tatcgaaaat cgtttattta tatatttgat   4320

gattatccat tagagaaccc ttcaaaaaac tctccactca actctctctg gtcagctgtc   4380

tcttccccat tctctagggt tttcaagctc aacctcaagc tccactacga tctcttcttc   4440

ttctctaatc tcaggtctga atctctcctt cttcactatc tctgatgctt tttactgaat   4500

ctgattgagg aaactttcca ttttaggatt tgttgatcaa atacactcgg tttaagaatt   4560

aggatcattc tcttttcgat ctagtttcat tagactcgtt cttttagctc ttgattttat   4620

agatctcgtt ttgaggaact gattatttgg ttgttgacag ttgaaagatg caaggtgtga   4680

ttcgatcctt cgtctccggt ggaaatgttg tgaaaggctc tgtgctgcaa catctccgtg   4740

tgattaaccc ggcgattcag ccttctgtgt tttgttcacg ctctgaatca actcaacctg   4800

cacgtatgga ggaatctgga ttcgagagca caactatttc cgatgtcatg aaatccaaag   4860

gcaaaagtgc tgatggatct tggctttggt gtactactga tgacactgtt tatgatgctg   4920

ttaaatccgt atgcttatac tactctcttt ttcctttttt agatatctcg atgtggattt   4980

ggaattgatt gtgtttgatt ttgtttagat gacacaacac aatgttggtg ccttggtggt   5040

tgtgaaacct ggtgagcaac aagctcttgc tggtatcatt acagagagag gtaaaattag   5100

atctaatcat taataatttt tttgttgtgt cttgtggtat gtgtgattca cttttcggca   5160

ttgtgatttc tctaga                                                    5176
```

<210> SEQ ID NO 7
<211> LENGTH: 1053
<212> TYPE: DNA
<213> ORGANISM: Arabidopsis thaliana
<220> FEATURE:
<221> NAME/KEY: misc_feature
<222> LOCATION: (1)...(1053)
<223> OTHER INFORMATION: n = A,T,C or G

<400> SEQUENCE: 7

```
acttctctan ggaaaactcn ngcccaggng nnagctgagt acgccatgca ggtaccgggt     60

ctcggaattc ccgcggtcga cccacgcgtc cgctcaaaat tgccaccaac ttcaaatttc    120

tctcctttaa acctttctca atcatctttc ttctgccttg gaatcctgat catggcgtcg    180

tcttctctca cttcgaaatc cattctcgga tccaccaaac tcggttcttc ttctcttccc    240

tcggagctcc gtcgtctctc ttctcccgcc gttcagatct ctctccgtac ccaaaccagg    300

aagaacttcc agatacaagc tactggaagt tcatatggga ctcattttcg agtttcaact    360

tttggagaat cacatggagg aggagttggt tgtatcattg atggttgtcc tcctcgtatt    420

ccacttactg aatctgattt gcaattcgat ctcgatagaa ggaggcctgg tcagagcagg    480

atcacaactc ctagaaaaga gactgatact tgccggatat cgtctggagt ctctgaagga    540

atgacgacag gaacacctat ccatgtgttt gtaccaaaca cagatcagag aggacttgat    600

tacagtgaaa tgtcggttgc ctatagacca tcgcatgctg atgcaactta tgacatgaag    660

tatggtgtca gatcagtgca gggtggagga agatcttcag ctagagagac cattggaaga    720

gttgctcctg gagctttggg caagagaatt ttgaagcaat ttgcaggaac tgagaatctt    780

gcctatgtct cgcaagttca ccaatgtgta cttccagaag aattggtaga cacgagaatt    840

tacactccga cagatagaaa ataacattgt cagaagccct aaatccgaat aatccgaaaa    900

agagataact gcgaatgaat ccgtcaagag cataaggaaa tcttgttggt gggttttgac    960

ctgcattgtc ggaaatccca cttgggcttg taaacggtgt tcataaactg accagaactg   1020
```

caaaactgta ttcccaactc aacaaaggga ttg 1053

<210> SEQ ID NO 8
<211> LENGTH: 1207
<212> TYPE: DNA
<213> ORGANISM: Arabidopsis thaliana

<400> SEQUENCE: 8
acataaacga caccgtttga gtaacggcta attacccttc ttcaatacca ctgaccatgc 60
acgctttgta cagtggaata atagtgtaac aacgtttaga aatattgtaa agtaaaaaaa 120
aaaaaccaaa gaacattcaa aaacctttct actctactac caaagccata ttgtttattt 180
tgttgttgcc tcagtccagt cttctgagca agtactccac ttgaacctct tttgttaaag 240
gcatgatcca atctccatat aagtcaccaa ctaagatcgg actgattttg taaacatgag 300
attcattccc ttcttcttct tcttcttctt tctcctccat cccaactttc acttcttgcc 360
cgtatgttcg ggttttcatc tcaactctct tctttatcgc atcttccaca gtcgggaatg 420
tcagcatatc catcagtcga tccttatctt gtgctttgat ggcggactcg tatgcttcgg 480
gtgaggcttg aaatttagct tctgcaacaa atttaccgta atggattctc tttgagagac 540
actgaaggca gatagcgtca cagacagctg ttgagccgta gttaccatca tcgcctttct 600
tcacaagtct tggaacaagg tctctgaagt acatgttcca tatcttcttg tttatgttta 660
tcgaatcagc agcaaaatgc aacacctttg ggtactgaag aggaggcaac ataggctctg 720
gtagatcatc agggaagaaa ggatgttcat caggactctt aaacctacca accttagcgt 780
gaagcttctc agtgccttta accatgtact caaccaaaga accattgaaa ccatccatgt 840
caaaagcagt aggatcataa gtatcagcat tgtaacagta cttggctctc tccaatagcc 900
caaatataat gctgtcctct tgacggatca aagagtttct aataccttca agagtcaaac 960
tctcactctc atccactcgt ttcttccctg tcaacgatcc agcgagtgtc ataacggcgt 1020
gaacagagct ggttccagag cgtggctttg atggctgagg aagagaacaa cgaacagaga 1080
aagaagattt ggttgatgga agaggaagaa gagtggaaat gggtgttgag gttgataatt 1140
cacgtcgatg gtcgaagaac ccaccaatcg cagaggagca acaagacgat ctcatcaaca 1200
atgacgc 1207

<210> SEQ ID NO 9
<211> LENGTH: 1006
<212> TYPE: DNA
<213> ORGANISM: Arabidopsis thaliana

<400> SEQUENCE: 9
tccttaaaat atcttacaaa atttaaaata gtgatgactg tgttgcttca ttcaattatt 60
ctatcatatc ctgacaaata tcaacaggcc cacttaaaaa cttaaggccc actttaacag 120
ggccagattt ggatacaaat aatattcaat cgagacgacg tagaagatac tcaacctcaa 180
cgagcttagt gagagggata agccattccc cgtagatgcg agaggcaagc aatggatcca 240
ctttatactt cttcttactc tcatcgccat agccagagtt gaattttact tcttgtccaa 300
acgtttctgc tttcttctgc actctcttct taaccatttc ttctactttc tcaaacgtca 360
acagcttcat caaagcctct ctatcctgag cgcgaatcgc aggctcgtaa tcttgtggag 420
catctctgaa tttgacctca gctacaaatt taccgtagtg aatccttctc gaaagagctt 480
gtaaacaggc gagatcacta gcagcagttg atggatagtt gccatcatcg ccaggtttga 540

-continued

```
caaacaaagg aagcaattct ttaaagtaaa tatcccagat ttgtttgtta atgttaacag    600

atagagcctt agggtgcaaa gccgatggat atttgtgcgt aggaaaaacc gagtgaggaa    660

tgttctcaag gaagaaagga ttctcttccg ggtattcata tcttcctacc ttagcttgga    720

tgatttctgt ctctctgacg aaaaactcag tgagagaaga gaaacttcca gaatctagac    780

aacgagattc ctcgaaagca ggagaattga gtggaaactt agctctctcg atcaagctga    840

agacgatggt gtcttcttgc ctaatcaacg attctctgat taagtcaaga ctcagtacat    900

tggaacaacc agaacccgaa tccgattcga agactcttgc catgccgctt caactgtatc    960

ccctggaaaa atgaagcttt cttcttcttc ttcctcaatg ctaaag                  1006
```

<210> SEQ ID NO 10
<211> LENGTH: 1217
<212> TYPE: DNA
<213> ORGANISM: Arabidopsis thaliana

<400> SEQUENCE: 10

```
cgagctacgt cagggttttt taataaaatc aacttgactt gctagcttgc gcagcttatg     60

tcaacattat ggttttcgga aaaataggat caatacaaat gttatgcttc cttctttgaa    120

aacattaatc cagtcttcta agcaagtact caatttggac ttcctttgtg aggggcatga    180

tcctttctcc atagagtttt gcaactaagc taggttgtat tttgtaggaa ggatcagctt    240

cagtttctgg gtcgttaatc gttatgtctt gaccaaaaat tctggctttg atctcaactc    300

tcttcttgac tacttcttca accgtttcgt acgttagaag ttgcatcagc tgtgtccggt    360

cttgttcttt gatagctgtt tcataggcag caggattttc acgaaacttg gcgtcagcaa    420

caaatttacg caagtgaatt ctctttgaaa gtatctgcaa acacattgtg tcacagagag    480

cagctgaacc acaattaccg tcatcccctg gcttgaccag tctggggaga aggtgtttga    540

aatacatatt ccacaccttc ttgttgatgt ttatcgattc ggcgcaacga tgcaaaacct    600

gtgggtattg aataggagga aggataggtt caggcaagca ttgtgggaaa aagggatgct    660

catcaggact cttgtacctg tccacctttg cgtgaagctt ttcagtttct ctgaccataa    720

actcaactaa agatccttga aacccttcca tagtaaaggc atcctcgtca taagtatcag    780

cgttgtagcg atactgagct cgttcaagaa gattaaagat aatactgtcc tcttgacgaa    840

tcaaagagtg tctaatgctt tcaagtttca aatactcact ctcatctacc cttagtagcc    900

ccctagagta tcggatcgga gaagctgcgg agagacggag gaagagagac ccagaagata    960

gtccaacttt tgatttatcg ttccagattg ataatcgcga gatgagtctt gaagaattcg   1020

taagattgag gtttggggaa ttgtaaaacg cgggtttgag taacttagcc tccatcggag   1080

aatcaaaaga ggaagagaca gagacagaga gtggagaaag aaaaggacag aggaacggat   1140

tcggcggagt taggaaaaat aaaaatcgga tagtgacaca aaaaaatcca atccgttaca   1200

aaattatctg gtcgaga                                                  1217
```

<210> SEQ ID NO 11
<211> LENGTH: 198
<212> TYPE: DNA
<213> ORGANISM: Artificial Sequence
<220> FEATURE:
<223> OTHER INFORMATION: Artificial promoter comprising a multiple cloning site (PacI, AscI, SwaI), TATTA box and 4X Gal4 upstream activation site.

<400> SEQUENCE: 11

```
ttaattaatc cgggcgcgcc tgatttaaat tggagctcca tggtttaaac tattgatcct     60
```

-continued

```
tcaaatggga atgaacccct ccttatatag aggactgcag ggggatctcg gaggagagtc    120

ttccggatct cggaggagag tcttccggat ctcggaggag agtcttccgg atctcggagg    180

agagtcttcc ggatcccc                                                  198
```

METHODS AND COMPOSITIONS FOR THE MODULATION OF CHORISMATE SYNTHASE AND CHORISMATE MUTASE EXPRESSION OR ACTIVITY IN PLANTS

CROSS REFERENCES TO RELATED APPLICATIONS

This application is a divisional of copending U.S. patent application Ser. No. 09/610,040, filed on Jul. 5, 2000, now U.S. Pat. No. 6,465,217.

FIELD OF THE INVENTION

The invention relates generally to plant molecular biology. In particular, the invention relates to compositions and methods for the regulation of plant growth and development through the modulation of either chorismate synthase or chorismate mutase gene expression or activity.

BACKGROUND OF THE INVENTION

Chorismate is an essential substrate for the synthesis of p-aminobenzoate, folate, ubiquinone and the aromatic amino acids tryptophan, phenylalanine and tyrosine. Chorismate is produced in the seventh step of the shikimate pathway. This pathway has been described in numerous publications. See, for example, *Shikimic Acid: Metabolism and Metabolites*, John Wiley & Sons, Winchester, UK, 1993. The first four steps of the shikimate biosynthetic pathway lead to the production of shikimate. Shikimate is then converted to chorismate in next three steps of the pathway. First, shikimate is converted to shikimate-5-phosphate by shikimate kinase. Next, 3-enolpyruvateshikimate 5-phosphate synthase converts shikimate-5-phosphate to 5-enolpyruvylshikimate 3-phosphate, which is then converted to chorismate by the enzyme chrosimate synthase.

The pathway leading to aromatic amino acid synthesis branches at chorismate. One branch leads to the synthesis of tryptophan. The other branch leads to the synthesis of phenylalanine and tyrosine. Thus, chorismate is the last common intermediate in the synthesis of tryptophan, phenylalanine and tyrosine.

In the branch leading to phenylalanine and tyrosine synthesis, chorismate is converted to prephenate by the enzyme chorismate mutase. Prephenate is the last common intermediate for biosyntheses of phenylalanine and tyrosine by two independent pathways that are present in both eukaryotes and prokaryotes.

Three isozymes of chorismate mutase, CM-1, CM-2 and CM-3 have been found in plants. Mobley et al. (1999) *Gene* 240:115–123. CM-1 and CM-3 are plastidic, while CM-2 is cytosolic. In *Arabidopsis thaliana*, CM-1 has 53% amino acid similarity with CM-2 and 68% amino acid similarity with CM-3.

The conversion of shikimate-5-phosphate to 5-enolpyruvylshikimate 3-phosphate is blocked by the commercially successful herbicide Roundup™ (glyphosate). Accordingly, the shikimate pathway has been considered an attractive target for herbicides (PCT publication WO 00/05353, the contents of which are incorporated by reference, and Roberts et al. (1998) *Nature* 393:801–805). However, while it has been suggested that that chorismate synthase could be a candidate for a herbicide target (Bomemann et al. (1985) *J Biol Chem* 270:228111–22815), previous studies have not been able to ascertain whether chorismate synthase or chorismate mutase are essential for plant growth, which is a key parameter for determining potential herbicide targets. Nor are there any herbicides that are known to act by modifying the activity of either of these enzymes. Thus, it is necessary to determine whether such enzymes are critical to plant growth, before they can be considered useful targets in assays for the identification of herbicides and herbicide candidates.

SUMMARY OF THE INVENTION

The present inventors have discovered that chorismate mutase and chorismate synthase are essential for plant growth. Specifically, the inhibition of chorismate mutase or chorismate synthase gene expression in plant seedlings results in severe chlorosis, reduced growth and developmental abnormalities. Thus, in one aspect, the present invention provides compositions for the modulation of plant growth or development comprising chorismate synthase and chorismate mutase antisense and sense polynucleotides, dsRNA and ribozymes, and related expression cassettes and vectors. The compositions of the invention are particularly useful for the modulation and inhibition of plant growth. The invention further provides plants, plant cells, and seeds containing the polynucleotides of the invention.

The inventors have proven that chorismate synthase and chorismate mutase can be used as targets for the identification of herbicides. Thus, the present invention also provides methods for the identification of chemicals that modulate chorismate synthase and chorismate mutase biochemical reactions. The methods of the invention are useful for the identification of herbicides and for the inhibition of plant growth and development. In addition, the methods of the invention are useful for the identification of compounds that stimulate the expression or function of chorismate synthase or chorismate mutase expression or function. Such compounds can be used to promote or manipulate plant growth and development.

BRIEF DESCRIPTION OF THE DRAWINGS

FIG. 1 is a diagram of the driver expression cassette.

DETAILED DESCRIPTION OF THE INVENITON

Definitions

Figure 2:
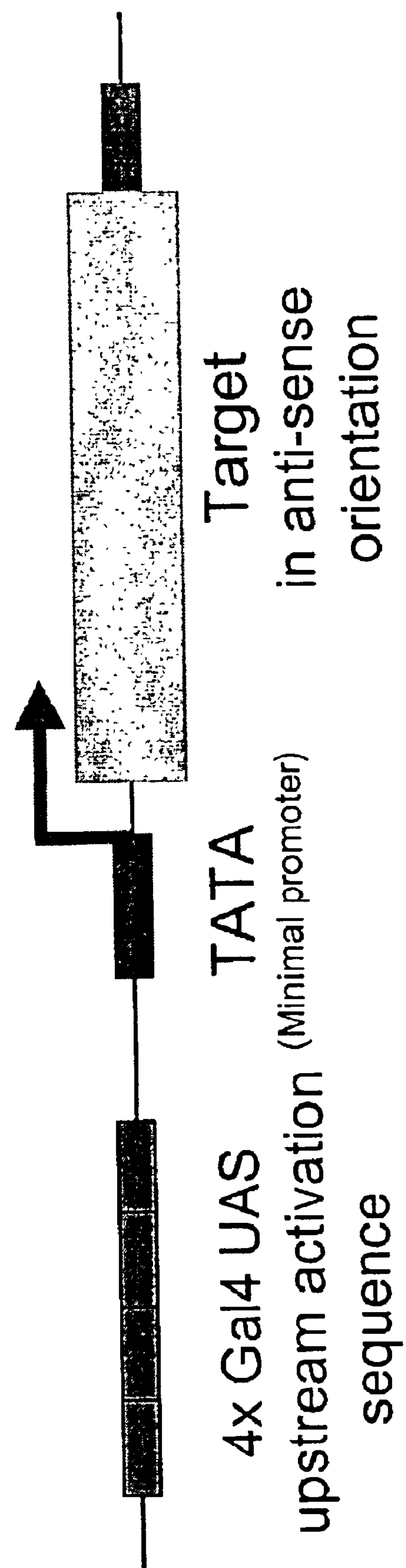
FIG. 2 is a diagram of the target expression cassette.

The term "antisense", for the purposes of the invention, refers to a nucleic acid comprising a polynucleotide which is sufficiently complementary to all or a portion of a chorismate synthase gene, chorismate mutase gene, primary transcripts or processed mRNAs derived from chorismate synthase or chorismate mutase genes, so as to interfere with expression of the endogenous chorismate synthase or chorismate mutase genes.

The term "binding" refers to a noncovalent interaction that holds two molecules together. For example, two such molecules could be an enzyme and an inhibitor of that enzyme. Noncovalent interactions include hydrogen bonding, ionic interactions among charged groups, van der Waals interactions and hydrophobic interactions among nonpolar groups. One or more of these interactions can mediate the binding of two molecules to each other.

As used herein, the term "chorismate" is synonymous with "chorismic acid". The structure is shown as entry number 2274 in the *Merck Index, Twelfth Edition*, Budavari et al., Eds., Merck Research Laboratories, Whitehouse Station, N.J., 1996.

"Complementary" polynucleotides are those which are capable of base-pairing according to the standard Watson-Crick complementarity rules. Specifically, purines will base pair with pyrimidines to form combinations of guanine paired with cytosine (G:C) and adenine paired with either thymine (A:T) in the case of DNA, or adenine paired with uracil (A:U) in the case of RNA. Two polynucleotides may hybridize to each other if they are complementary to each other, or if each has at least one region that is substantially complementary to the other.

The structure of "5-enolpyruvylshikimate 3-phosphate" is shown in Macheroux et al. (1996) *J Biol Chem* 271:25850–25858.

The term "herbicide", as used herein, refers to a chemical that may be used to kill or suppress the growth of at least one plant, plant cell, plant tissue or seed.

By "herbicidally effective amount" is meant an amount of a chemical or composition sufficient to kill a plant or decrease plant growth and/or viability by at least 10%. More preferably, the growth or viability will be decreased by 25%, 50%, 75%, 80%, 90% or more.

For the purposes of the invention, "high stringency hybridization conditions" refers to hybridization in 50% formamide, 1 M NaCL, 1% SDS at 37° C., and a final wash in 0.1×SSC at 60° C. Methods for nucleic acid hybridizations are described in Meinkoth and Wahl (1984) *Anal Biochem* 138:267–284; *Current Protocols in Molecular Biology*, Chapter 2, Ausubel et al. Eds., Greene Publishing and Wiley-Interscience, New York, 1995; and Tijssen, *Laboratory Techniques in Biochemistry and Molecular Biology: Hybridization with Nucleic Acid Probes*, Part I, Chapter 2, Elsevier, N.Y., 1993.

The term "inhibitor", as used herein, refers to a chemical substance that inactivates the enzymatic activity of chorismate synthase or chorismate mutase. The inhibitor may function by interacting directly with the enzyme, a cofactor of the enzyme, the substrate of the enzyme, or any combination thereof.

A polynucleotide may be "introduced" into a plant cell by any means, including transfection, transformation or transduction, electroporation, particle bombardment, Agroinfection and the like. The introduced polynucleotide may be maintained in the cell stably if it is incorporated into a non-chromosomal autonomous replicon or integrated into the plant chromosome. Alternatively, the introduced polynucleotide may be present on an extra-chromosomal non-replicating vector and be transiently expressed or transiently active.

For the purposes of the invention, an "isolated polynucleotide" is a polynucleotide that is substantially free of the nucleic acid sequences that normally flank the polynucleotide in it naturally occurring replicon. For example, a cloned polynucleotide is considered isolated. Alternatively, a polynucleotide is considered isolated if it has been altered by human intervention, or placed in a locus or location that is not its natural site, or if it is introduced into cell by agroinfection.

By "male tissue" is meant the tissues of a plant that are directly involved or supportive of the reproduction of the male gametes. Such tissues include pollen tapetum, anther, tassel, pollen mother cells and microspores. A "male tissue-preferred" or "male tissue-specific" promoter will be expressed predominantly in one or more male tissues. It is possible that a male tissue preferred promoter will be expressed in non-male tissues, however, expression will usually be at a lower level than in male tissues.

As used herein, "nucleic acid" and "polynucleotide" refers to RNA or DNA that is linear or branched, single or double stranded, or a hybrid thereof. The term also encompasses RNA/DNA hybrids. Less common bases, such as inosine, 5-methylcytosine, 6-methyladenine, hypoxanthine and others can also be used for antisense, dsRNA and ribozyme pairing. For example, polynucleotides which contain C-5 propyne analogues of uridine and cytidine have been shown to bind RNA with high affinity and to be potent antisense inhibitors of gene expression. Other modifications, such as modifications to the phosphodiester backbone, or the 2'-hydroxy in the ribose sugar group of the RNA can also be made. The antisense polynucleotides and ribozymes can consist entirely of ribonucleotides, or can contain mixed ribonucleotides deoxyribonucleotides. The polynucleotides of the invention may be produced by any means, including genomic preparations, cDNA preparations, in vitro synthesis, RT-PCR and in vitro or in vivo transcription.

By "operably linked" is meant that a polynucleotide is functionally linked to a promoter, so that the transcription of the polynucleotide can be initiated from the promoter.

The "percent sequence identity" between two polynucleotide or two polypeptide sequences is determined according to the either the BLAST program (Basic Local Alignment Search Tool; Altschul and Gish (1996) *Meth Enzymol* 266:460–480 and Altschul (1990) *J Mol Biol* 215:403–410) in the Wisconsin Genetics Software Package (Devererreux et al. (1984) *Nucl Acid Res* 12:387), Genetics Computer Group (GCG), Madison, Wis. (NCBI, Version 2.0.11, default settings) or using Smith Waterman Alignment (Smith and Waterman (1981) *Adv Appl Math* 2:482) as incorporated into GeneMatcher Plus™ (Paracel, Inc., http://www.paracel.com/html/genematcher.html; using the default settings and the version current at the time of filing). It is understood that for the purposes of determining sequence identity when comparing a DNA sequence to an RNA sequence, a thymine nucleotide is equivalent to a uracil nucleotide.

"Plant" refers to whole plants, plant organs and tissues (e.g., stems, roots, ovules, stamens, leaves, embryos, meristematic regions, callus tissue, gametophytes, sporophytes, pollen, microspores and the like) seeds, plant cells and the progeny thereof.

By "plant chorismate mutase RNA" is meant a primary transcript or processed mRNA derived from any plant chorismate mutase gene.

By "plant chorismate synthase RNA" is meant a primary transcript or processed mRNA derived from any plant chorismate synthase gene.

By "polypeptide" is meant a chain of at least four amino acids joined by peptide bonds. The chain may be linear, branched, circular or combinations thereof. The polypeptides may contain amino acid analogs and other modifications, including, but not limited to glycosylated or phosphorylated residues.

As used herein, the term "prephenate" is synonymous with "prephenic acid". The structure is shown as compound number 7920 in the *Merck Index, Twelfth Edition*, Budavari et al., Eds., Merck Research Laboratories, Whitehouse Station, N.J., 1996.

As used herein, the term "probe" refers to can have no more than an additional 10 nucleic acid residues at either end of a polynucleotide having a defined sequence.

For the purposes of the invention, "recombinant polynucleotide" refers to a polynucleotide that has been altered, rearranged or modified by genetic engineering. Examples include any cloned polynucleotide, and polynucleotides that are linked or joined to heterologous sequences. Two polynucleotide sequences are heterologous if they are not naturally found joined together. The term recombinant does not refer to alterations to polynucleotides that result from naturally occurring events, such as spontaneous mutations.

By "ribozyme" is meant a catalytic RNA-based enzyme capable of targeting and cleaving particular base sequences in both DNA and RNA. Ribozymes comprise a polynucleotide sequence that is complementary to a portion of a target nucleic acid and a catalytic region that cleaves the target nucleic acid. Ribozymes can be designed that specifically pair with and inactivate a target RNA by catalytically cleaving the RNA at a targeted phosphodiester bond. Methods for making and using ribozymes are known to those skilled in the art. See, for example, U.S. Pat. Nos. 6,025,167; 5,773,260 and 5,496,698, the contents of which are incorporated by reference, and in Haseloff and Gerlach (1988) *Nature* 334:586–591.

The term "specific binding" refers to an interaction between chorismate synthase or chorismate mutase and a molecule or compound, wherein the interaction is dependent upon the primary amino acid sequence or the conformation of chorismate synthase or chorismate mutase.

"Transform", as used herein, refers to the introduction of a polynucleotide (single or double stranded DNA, RNA, or a combination thereof) into a living cell by any means. Transformation may be accomplished by a variety of methods, including, but not limited to, agroinfection, electroporation, particle bombardment, and the like. This process may result in transient or stable (constitutive or regulated) expression of the transformed polynucleotide. By "stably transformed" is meant that the sequence of interest is integrated into a replicon in the cell, such as a chromosome or episome. Transformed cells, tissues and plants encompass not only the end product of a transformation process, but also the progeny thereof which retain the polynucleotide of interest.

For the purposes of the invention, "transgenic" refers to any plant, plant cell, callus, plant tissue or plant part, that contains all or part of at least one recombinant polynucleotide. In many cases, all or part of the recombinant polynucleotide is stably integrated into a chromosome or stable extra-chromosomal element, so that it is passed on to successive generations.

Embodiments of the Invention

The present inventors have discovered that inhibition of chorismate synthase or chorismate mutase gene expression strongly inhibits the growth and development of plant seedlings. Thus, the inventors are the first to show that chorismate synthase and chorismate mutase are targets for herbicides.

Accordingly, the invention provides methods for identifying compounds that modulate chorismate synthase or chorismate mutase gene expression or activity. Such methods include ligand binding assays, assays for enzyme activity and assays for chorismate synthase and chorismate mutase gene expression. The compounds identified by the methods of the invention are useful for the modulation of plant growth and development.

Any compound that is a ligand for chorismate synthase, other than its substrate, 5-enolpyruvylshikimate 3-phosphate, may have herbicidal activity. For the purposes of the invention, "ligand" refers to a molecule that will bind to a site on a polypeptide. Thus, in one embodiment, the invention provides a method for identifying a compound as a candidate for a herbicide, comprising:

a) combining said compound with at least one polypeptide selected from the group consisting of: a plant chorismate synthase, a polypeptide comprising at least ten consecutive amino acids of a plant chorismate synthase, a polypeptide having at least 85% sequence identity with a plant chorismate synthase, and a polypeptide having at least 80% sequence identity with a plant chorismate synthase and at least 50% of the activity thereof; and b) detecting the presence and/or absence of binding between said compound and said polypeptide;

wherein binding indicates that said compound is a candidate for a herbicide.

Similarly, any compound that is a ligand for chorismate mutase, other than its substrate, chorismate, may have herbicidal activity. Thus, in another embodiment, the invention provides a method for identifying a compound as a candidate for a herbicide, comprising:

a) combining said compound with at least one polypeptide selected from the group consisting of: a plant chorismate mutase, a polypeptide comprising at least ten consecutive amino acids of a plant chorismate mutase, a polypeptide having at least 85% sequence identity with a plant chorismate mutase and a polypeptide having at least 80% sequence identity with a plant chorismate mutase and at least 50% of the activity thereof; and b) detecting the presence and/or absence of binding between said compound and said polypeptide;

wherein binding indicates that said compound is a candidate for a herbicide.

By "plant chorismate synthase" and "plant chorismate mutase" is meant the polypeptide corresponding to chorismate synthase or chorismate mutase, respectively, that can be found in at least one plant. The chorismate synthase may be from any plant, including both monocots and dicots. In various embodiments, the chorismate synthase or chorismate mutase is from barnyard grass (*Echinochloa crus-galli*), crabgrass (*Digitaria sanguinalis*), green foxtail (*Setana viridis*), perennial ryegrass (*Lolium perenne*), hairy beggarticks (*Bidens pilosa*), nightshade (*Solanum nigrum*), smartweed (*Polygonum lapathifolium*), velvetleaf (*Abutilon theophrasti*), common lambsquarters (*Chenopodium album* L.), *Brachiara plantaginea, Cassia occidentalis, Ipomoea aristolochiaefolia, Ipomoea purpurea, Euphorbia heterophylla*, Setaria spp, *Amaranthus retroflexus, Sida spinosa, Xanthium strumarium* and the like. In one embodiment, the chorismate synthase or chorismate mutase is an Arabidopsis chorismate synthase, chorismate mutase-1, or chorismate mutase-3.

Fragments of a plant chorismate synthase or chorismate mutase may be used in the methods of the invention. The fragments comprise at least 5 consecutive amino acids of a plant chorismate synthase or a plant chorismate mutase. Preferably, the fragment comprises at least 6, 7, 8, 9, 10, 15, 20, 25, 30, 35 or at least 40 consecutive amino acids residues of a plant chorismate synthase or chorismate mutase.

Polypeptides having at least 80% sequence identity with a plant chorismate mutase or a plant chorismate synthase are also useful in the methods of the invention. Preferably, the sequence identity is at least 85%, more preferably the identity is at least 90%, most preferably the sequence identity is at least 95%.

In addition, it is preferred that the polypeptide has at least 50% of the activity of a plant chorismate synthase or chorismate mutase. More preferably, the polypeptide has at least 60%, at least 70%, at least 80% or at least 90% of the activity of a plant chorismate synthase or chorismate mutase.

Preferably, the activity of the polypeptide is compared to the activity of the Arabidopsis chorismate synthase polypeptide or an Arabidopsis chorismate mutase-1 polypeptide. For the purposes of the invention, chorismate synthase activity refers to the ability to convert 5-enolpyruvateshikimate 3-phosphate to chorismate. Chorismate mutase activity refers to the ability to convert chorismate to prephenate. Methods for measuring chorismate synthase and chorismate mutase activity are known in the art. Preferably, chorismate synthase activity is measured according to the method described in Henstrand et al. (1995) *J Biol Chem* 270:20447–20452. In another preferred embodiment, chorismate mutase activity is measured according to the method described in Krappmann et al. (1999) *J Biol Chem* 274:22275–22282.

Any technique for detecting the binding of a ligand to its target may be used in the methods of the invention. Preferably, the ligand and target are combined in a buffer. Polypeptides and proteins that can reduce non-specific binding, such as BSA or protein extracts from cells that do not produce the target, may be included in binding assay.

Many methods for detecting the binding of a ligand to its target are known in the art, and include, but are not limited to the detection of an immobilized ligand-target complex or the detection of a change in the properties of a target when it is bound to a ligand. For example, in one embodiment, an array of immobilized candidate ligands is provided. The immobilized ligands are contacted with a plant chorismate synthase protein or a fragment or variant thereof, the unbound protein is removed and the bound chorismate synthase is detected. In a preferred embodiment, bound chorismate synthase is detected using a labeled binding partner, such as a labeled antibody. In a variation of this assay, chorismate synthase is labeled prior to contacting the immobilized candidate ligands. Preferred labels include fluorescent or radioactive moieties. Preferred detection methods include fluorescence correlation spectroscopy (FCS) and FCS-related confocal nanofluorimetric methods. See http://www.evotec.de/technology. The same methods are applicable to the detection of binding of a candidate ligand to chorismate mutase.

Once a compound is identified as a candidate for a herbicide, it can be tested for the ability to inhibit or otherwise modulate chorismate mutase or chorismate synthase enzyme activity. The compounds can be tested using either in vitro or cell based enzyme assays. Alternatively, a compound can be tested by applying it directly to a plant or plant cell, or expressing it therein, and monitoring the plant or plant cell for changes or decreases in growth, development, viability or alterations in gene expression.

Thus, in one embodiment, the invention provides a method for determining whether a compound identified as a herbicide candidate by an above method has herbicidal activity, comprising: contacting a plant or plant cells with said herbicide candidate and detecting the presence or absence of a decrease in the growth or viability of said plant or plant cells.

By decrease in growth, is meant that the herbicide candidate causes at least a 10% decrease in the growth of the plant or plant cells, as compared to the growth of the plants or plant cells in the absence of the herbicide candidate. By a decrease in viability is meant that at least 10% of the plants cells, or portion of the plant contacted with the herbicide candidate are nonviable. Preferably, the growth or viability will be at decreased by at least 20%. More preferably, the growth or viability will be decreased by at least 50%, 75% or at least 90% or more. Methods for measuring plant growth and cell viability are known to those skilled in the art. Clearly, it is possible that a candidate compound may have herbicidal activity only for certain plants or certain plant species.

The ability of a compound to inhibit or modulate chorismate synthase or chorismate mutase activity can be detected using in vitro enzymatic assays in which the disappearance of a substrate or the appearance of a product is detected. Chorismate synthase converts 5-enolpyruvylshikimate 3-phosphate to chorismate. Chorismate mutase converts chorismate to prephenate. Methods for detection of these substrates and products, such as mass spectroscopy and reverse phase HPLC, are known to those skilled in the art.

Thus, the invention provides a method for identifying a compound as a candidate for a herbicide, comprising:

a) combining 5-enolpyruvylshikimate 3-phosphate and chorismate synthase under reaction conditions suitable for chorismate synthase activity;

b) combining 5-enolpyruvylshikimate 3-phosphate, chorismate synthase and said compound under the reaction conditions of step (a);

c) detecting the amount of 5-enolpyruvyishikimate 3-phosphate and/or chorismate in steps (a) and (b).

In this method, if a candidate compound inhibits chorismate synthase activity, a higher concentration of the precursor (5-enolpyruvylshikimate 3-phosphate) and a lower level of the product (chorismate) will be detected in the presence of the candidate compound (step b) than in the absence of the compound (step a).

Preferably the chorismate synthase is a plant chorismate synthase.

Enzymatically active fragments of a plant chorismate synthase are also useful in the methods of the invention. For example, a polypeptide comprising at least ten consecutive amino acid residues of a plant chorismate synthase may be used in the methods of the invention. In addition, a polypeptide having at least 80%, 85%, 90%, 95%, 98% or at least 99% sequence identity with a plant chorismate synthase may be used in the methods of the invention. Also, polypeptides having at least 80% sequence identity with at least 15 consecutive amino acid residues of a plant chorismate synthase are also useful in the methods of the invention. Preferably, the polypeptide has at least 80% sequence identity with a plant chorismate synthase and at least 50%, 75%, 90% or at least 95% of the activity thereof.

Thus, the invention provides a method for identifying a compound as a candidate for a herbicide, comprising:

a) combining, under reaction conditions suitable for chorismate synthase activity, 5-enolpyruvylshikimate 3-phosphate and a polypeptide selected from the group consisting of: a polypeptide having at least 85% sequence identity with a plant chorismate synthase, a polypeptide having at least 80% sequence identity with a plant chorismate synthase and at least 50% of the activity thereof, and a polypeptide comprising at least 10 consecutive amino acids of a plant chorismate synthase;

b) combining 5-enolpyruvylshikimate 3-phosphate, said polypeptide and said compound under the reaction conditions of step (a);

c) detecting the amount of 5-enolpyruvylshikimate 3-phosphate and/or chorismate in steps (a) and (b).

Again, if a candidate compound inhibits chorismate synthase activity, a higher concentration of the precursor (5-enolpyruvylshikimate 3-phosphate) and a lower level of the product (chorismate) will be detected in the presence of the candidate compound (step b) than in the absence of the compound (step a).

These methods are useful for identifying compounds that inhibit chorismate synthase activity. Other assays for chorismate synthase activity are known in the art. See for example, Ramjee et al. (1994) *Anal Biochem* 220:137–141; and Macheroux et al. (1996) *J Biol Chem* 271:25850–25858. For example, in one assay, chorismate synthase activity is measured by monitoring the appearance of chorismate at 275 nm at 30° C. in a reaction volume of 0.5 ml containing triethanolamine-HCL, pH 8.0, 50 mM KCl, 2.5 mM $MgCl_2$, 200 μM NADPH, 10 μM FMN and 80 μM 5-enolpyruvyishikimate 3-phosphate (EPSP). Henstrand et al. (1991) *J Biol Chem* 270:20447–20452.

Similar methods can be used to identify inhibitors of chorismate mutase activity. Chorismate mutase converts chorismate to prephenate. Thus, in another embodiment, the invention provides a method for identifying a compound as a candidate for a herbicide, comprising:

a) combining chorismate and chorismate mutase under reaction conditions suitable for chorismate mutase activity;

b) combining chorismate, chorismate mutase and said compound under the reaction conditions of step (a);

c) detecting the amount of chorismate and/or prephenate in steps (a) and (b).

If a candidate compound inhibits chorismate mutase activity, a higher concentration of the precursor (chorismate) and a lower level of the product (prephenate) will be detected in the presence of the compound (step b) than in the absence of the compound (step a).

Preferably the chorismate mutase is a plant chorismate mutase. More preferably, the chorismate mutase is a plant chorismate mutase-1 or plant chorismate mutase-3. In one embodiment, a polypeptide comprising at least ten consecutive amino acid residues of a plant chorismate mutase may be used in the methods of the invention. In addition, a polypeptide having at least 80%, 85%, 90%, 95%, 98% or at least 99% sequence identity with a plant chorismate mutase may be used in the methods of the invention. Preferably, the polypeptide has at least 80% sequence identity with a plant chorismate mutase and at least 50%, 75%, 90% or at least 95% of the activity thereof.

Thus, in another aspect, the invention provides a method for identifying a compound as a candidate for a herbicide, comprising:

a) combining, under reaction conditions suitable for chorismate mutase activity, chorismate and a polypeptide selected from the group consisting of: a polypeptide having at least 85% sequence identity with a plant chorismate mutase, a polypeptide having at least 80% sequence identity with a plant chorismate mutase and at least 50% of the activity thereof, and a polypeptide comprising at least 10 consecutive amino acids of a plant chorismate mutase;

b) combining chorismate, said polypeptide and said compound under the reaction conditions of step (a);

c) detecting the amount of prephenate and/or chorismate in steps (a) and (b).

These methods are useful for identifying compounds that inhibit chorismate mutase activity. Other assays for chorismate mutase are known in the art. See, for example, Krappmann et al. (1999) *J Biol Chem* 274:22275–22282; Gilchrist and Connelly (1987) *Methods in Enzymology* 142:450–463; Schmidheini et al. (1989) *J Bacteriol* 171:1245–1253; Gorisch (1978) *Anal Biochem* 86:764–768; and Gorisch (1987) *Methods in Enzymology* 142:463.

One assay commonly used to measure chorismate mutase activity is based on the spectrophotometric estimation of phenylpyruvate obtained by acid conversion of the reaction product of prephenate. Metzenberg and Mitchell (1954) *Arch Biochem and Biophys* 243:374. In this assay, phenylpyruvate is estimated by the absorbance of either the enol-tautomer in alkaline solution (E=17,500 $M^{-1}$ $cm^{-1}$ at 320 nm in 1 M NaOH) or the enol-borate complex in either a concentrated solution of sodium borate and arsenate or phosphate (E=9292 $M^{-1}$ $cm^{-1}$ at 300 nm). Alternatively, the disappearance of chorismate may be assayed spectrophotometrically. Nishioka and Woodin (1972) *Anal Biochem* 45:617. The details of these assays and their advantages and disadvantages are described in Gilchrist and Connelly (1987) *Methods in Enzymology* 142:450–463.

For the in vitro enzymatic assays, chorismate synthase and chorismate mutase proteins may be purified from a plant or may be recombinantly produced in and purified from a plant, bacteria, or eukaryotic cell culture. Preferably these proteins are produced using a baculovirus expression system. Methods for the purification of chorismate synthase are described in White et al. (1988) *Biochem J* 251:313–322; Henstrand et al. (1995) *J Biol Chem* 270:20447–20452; Bornemann et al. (1995) *Biochem J* 305:707–710. Methods for the purification of chorismate mutase are disclosed in Krappmann et al. (1999) *J Biol Chem* 274:22275–22282; Schmidheini et al. (1990) *Biochem* 29:3660–3669; and Gilchrist and Connelly (1987) *Methods in Enzymology* 142:450–463. In a preferred method, a 6×histidine tagged chorismate synthase fusion protein or a 6×histidine tagged chorismate mutase fusion protein is affinity purified. See, for example, Grundy et al. (1998) *Protein Expr Purif* 13:61–66; and Hosfield and Lu (1999) *Biotechniques* 27:58–60.

As an alternative to in vitro assays, the invention also provides plant and plant cell based assays. In one embodiment, the invention provides a method for identifying a chemical as a candidate for a herbicide, comprising:

a) measuring the expression of chorismate synthase and/or chorismate mutase in a plant or plant cell in the absence of said chemical;

b) contacting a plant or plant cell with said chemical and measuring the expression of chorismate synthase and/or chorismate mutase in said plant or plant cell;

c) comparing the expression of chorismate synthase and/or chorismate mutase in steps (a) and (b).

A reduction in chorismate synthase or chorismate mutase expression indicates that the compound is a herbicide candidate. In one embodiment, the plant or plant cell is an *Arabidopsis thaliana* plant or plant cell.

Expression of chorismate synthase can be measured by detecting chorismate synthase primary transcript or mRNA, chorismate synthase polypeptide or chorismate synthase enzymatic activity. Similarly, expression of chorismate mutase can be measured by detecting chorismate mutase primary transcript or mRNA, chorismate mutase polypeptide or chorismate mutase enzymatic activity.

Methods for detecting the expression of RNA and proteins are known to those skilled in the art. See, for example, *Current Protocols in Molecular Biology* Ausubel et al., eds., Greene Publishing and Wiley-Interscience, New York, 1995. The method of detection is not critical to the invention.

Methods for detecting chorismate synthase or chorismate mutase RNA include, but are not limited to amplification assays such as quantitative PCR, and/or hybridization assays such as Northern analysis, dot blots, slot blots, in-situ hybridization, bDNA assays and microarray assays.

Methods for detecting protein expression include, but are not limited to, immunodetection methods such as Western blots, His Tag and ELISA assays, polyacrylamide gel electrophoresis, mass spectroscopy and enzymatic assays. For enzymatic assays, methods for detecting chorismate synthase and chorismate mutase activity are described above. Alternative methods have been described in the literature. Also, any reporter gene system may be used to detect chorismate synthase or chorismate mutase protein expression. For detection using gene reporter systems, a polynucleotide encoding a reporter protein is fused in frame with chorismate synthase or chorismate mutase, so as to produce a chimeric polypeptide. Methods for using reporter systems are known to those skilled in the art. Examples of reporter genes include, but are not limited to, chloramphenicol acetyltransferase (Gorman et al. (1982) *Mol Cell Biol* 2:1104; Prost et al. (1986) *Gene* 45:107–111), β-galactosidase (Nolan et al. (1988) *Proc Natl Acad Sci USA* 85:2603–2607), alkaline phosphatase (Berger et al. (1988) *Gene* 66:10), luciferase (De Wet et al. (1987) *Mol Cell Biol* 7:725–737), β-glucuronidase (GUS), fluorescent proteins, chromogenic proteins and the like.

Chemicals, compounds or compositions identified by the above methods as modulators of chorismate synthase or chorismate mutase expression or activity can then be used to control plant growth. For example, compounds that inhibit plant growth can be applied to a plant or expressed in a plant, in order to prevent plant growth. Thus, the invention provides a method for inhibiting plant growth, comprising contacting a plant with a compound identified by the methods of the invention as having herbicidal activity. Alternatively, such compounds may be applied to or expressed in a particular plant tissue or organ so as to modulate growth of that tissue or organ.

Herbicides and herbicide candidates identified by the methods of the invention can be used to control the growth of undesired plants, including both monocots and dicots. Examples of undesired plants include, but are not limited to barnyard grass (*Echinochloa crus-galli*), crabgrass (*Digitaria sanguinalis*), green foxtail (*Setana viridis*), perennial ryegrass (*Lolium perenne*), hairy beggarticks (*Bidens pilosa*), nightshade (*Solanum nigrum*), smartweed (*Polygonum lapathifolium*), velvetleaf (*Abutilon theophrasti*), common lambsquarters (*Chenopodium album* L.), *Brachiara plantaginea, Cassia occidentalis, Ipomoea aristolochiaefolia, Ipomoea purpurea, Euphorbia heterophylla, Setaria spp, Amaranthus retroflexus, Sida spinosa, Xanthium strumarium* and the like.

Having identified chorismate synthase and chorismate mutase as essential for plant growth and development, the invention provides compounds for the inhibition and modulation of plant growth. As described herein, antisense expression of chorismate synthase or chorismate mutase in plant seedlings results in extremely poor growth and developmental abnormalities. Accordingly, the invention provides polynucleotides that specifically inhibit the expression of chorismate synthase or chorismate mutase.

The polynucleotides of the invention are capable of specifically inhibiting transcription or translation of a plant chorismate synthase or chorismate mutase RNA, or decreasing the stability thereof. Such polynucleotides include, but are not limited to, antisense molecules, ribozymes, sense molecules, interfering double-stranded RNA (dsRNA) and the like.

The effect of the expression of such polynucleotides on plant growth and development will depend upon many factors, including but not limited to the specificity and activity of the polynucleotide, the level of expression of the polynucleotide and the expression pattern of the promoter driving the expression of a polynucleotide of the invention. For example, systemic expression of such polynucleotides can result in plant death or reduced growth. Inducible expression of such polynucleotides could result in plant death or decreased growth at the time of induction. Similarly, developmentally regulated expression could result in a reduction of growth or plant death at a particular stage of development.

Tissue specific expression would result in a necrosis or reduced growth of that tissue. In preferred embodiments, the polynucleotides of the invention are operably linked to a tissue-specific or tissue preferred promoter. In one embodiment, the polynucleotides of the invention are operably linked to a male-tissue preferred promoter. Male tissue-preferred expression of a polynucleotide of the invention can result in male-sterile plants. Female tissue-preferred expression of a polynucleotides of the invention can result in seedless plants, or in plants having reduced seed size.

While the polynucleotides of the invention are not limited to a particular mechanism of action, reduction in chorismate synthase or chorismate mutase gene expression can be mediated at the DNA level and at transcriptional, post-transcriptional, or translational levels. For example, it is thought that dsRNA suppresses gene expression by both a posttranscriptional process and by DNA methylation. Sharp and Zamore (2000) *Science* 287:2431–2433. Ribozyrnes specifically bind and catalytically cleave RNA. Gene specific inhibition of expression in plants by an introduced sense polynucleotide is termed "cosuppression".

Antisense polynucleotides, when introduced into a plant cell, are thought to specifically bind to their target polynucleotide and inhibit gene expression by interfering with transcription, splicing, transport, translation and/or stability. Reported mechanisms of antisense action include RNase H-mediated cleavage, activation or inhibition of splicing, inhibition of 5'-cap formation, translation arrest and activation of double strand RNases. See Crooke (1999) *Biochim Biophys Acta* 1489:31–44.

Antisense polynucleotides can be targeted to chromosomal DNA, to a primary RNA transcript or to a processed mRNA. Preferred target regions include splice sites and translation initiation and termination codons, and other sequences within the open reading frame.

Thus, in another aspect, the invention provides an isolated nucleic acid for modulating plant growth, comprising: a polynucleotide selected from the group consisting of a plant chorismate synthase-specific ribozyme, a plant chorismate synthase-specific antisense molecule, a plant chorismate synthase-specific dsRNA, a plant chorismate synthase-specific sense molecule, a plant chorismate mutase-specific ribozyme, a plant chorismate mutase-specific antisense molecule, a plant chorismate mutase-specific dsRNA and a plant chorismate mutase-specific sense molecule.

In preferred embodiments, the polynucleotide is a plant chorismate synthase-specific antisense molecule or a plant chorismate mutase-specific antisense molecule. Thus, the invention provides an antisense molecule specific to all or a part a polynucleotide selected from the group consisting of: a chorismate synthase primary transcript, a chorismate synthase mRNA, a chorismate mutase primary transcript and a chorismate mutase mRNA; wherein said chorismate synthase mRNA is not from maize, soybean, wheat or rice.

Preferably the antisense molecule is specific for a plant chorismate synthase or chorismate mutase mRNA. In one embodiment, the antisense molecule is specific for an Arabidopsis chorismate synthase or chorismate mRNA. The present inventors are the first to provide the sequence of an Arabidopsis chorismate synthase partial cDNA (SEQ ID NO:1). SEQ ID NO:7 is the antisense or complement of SEQ ID NO:1 Thus, in one aspect, the invention provides an isolated polynucleotide selected from the group comprising:

a) a nucleotide sequence consisting essentially of SEQ ID NO:1 or SEQ ID NO:7;

b) a nucleotide sequence consisting essentially of a sequence having at least 80% sequence identity with SEQ ID NO:1 or SEQ ID NO:7; and c) a probe comprising SEQ ID NO:1 or SEQ ID NO:7.

The invention further provides vectors comprising these polynucleotides and related transformed cells and transformed plants.

The sequences of Arabidopsis chorismate mutase-1, chorismate mutase-2 and chorismate mutase-3 full length cDNAs are shown in SEQ ID NOs:2, 3, and 4, respectively. The sequence of the Arabidopsis chorismate mutase-1 and chorismate mutase-2 genes are shown in SEQ ID NOs:5 and 6, respectively. A preferred antisense polynucleotide that is specific for the Arabidopsis chorismate synthase mRNA is shown in SEQ ID NO:7. Antisense sequences corresponding to the Arabidopsis full length chorismate mutase-1, chorismate mutase-2 and chorismate mutase-3 cDNAs are shown in SEQ ID NOs:8, 9, and 10, respectively.

By "plant chorismate synthase-specific" and "plant chorismate mutase-specific" polynucleotides is meant that the polynucleotide can specifically hybridize to either the sense or antisense strand of a plant chorismate synthase or chorismate mutase gene or RNA. The terms plant "chorismate synthase RNA" or "chorismate mutase RNA" include both the primary transcript and the processed mRNA. For example, a portion of a ribozyme will hybridize with all or a portion of a target primary transcript or spliced mRNA. Similarly, all or a portion of an antisense molecule will hybridize with a target primary transcript or spliced mRNA. In contrast, a sense polynucleotide will have partial or complete sequence identity with all or a portion of a target gene and primary transcript or mRNA. Thus, the sense polynucleotide will hybridize to a complement of a target gene, primary transcript or mRNA. Obviously, a dsRNA, when denatured, will hybridize to both a target gene and/or mRNA and the corresponding complement.

By "specifically hybridize" is meant that the polynucleotide will hybridize to the target gene or RNA at a level of at least two-fold over background under conditions of high stringency. For example, a chorismate synthase-specific antisense polynucleotide will hybridize to a chorismate synthase gene, primary transcript and/or processed mRNA of at least one plant with a affinity of at least two fold over the level of hybridization to that plant's other nucleic acids.

The specificity of the hybridization will depend upon many factors, including the length and degree of complementarity between the antisense molecule and the target sequence, the length of the antisense molecule, the temperature of the hybridizations and washes, and the salt, detergent and formamide concentrations of the hybridization and wash buffers.

In preferred embodiments, the polynucleotides of the invention will hybridize to at least one plant chorismate synthase or chorismate mutase gene or RNA under high stringency hybridization conditions. Thus, in one embodiment, the invention provides an antisense molecule that hybridizes under high stringency conditions to SEQ ID NO:1, SEQ ID NO:2, SEQ ID NO:3, SEQ ID NO:4, SEQ ID NO:5 or SEQ ID NO:6.

It is understood that the polynucleotides of the invention need not be completely complementary to the target chorismate synthase or chorismate mutase gene or RNA, nor that they hybridize to each other along their entire length, in order to modulate expression or to form specific hybrids. Furthermore, the polynucleotides of the invention need not be full length with respect to the target plant chorismate synthase or chorismate mutase gene or RNA. In general, greater homology can compensate for shorter polynucleotide length.

Typically the polynucleotides of the invention will comprise a nucleotide sequence having 60–100% sequence identity with at least 14, 15, 16, 17, 18, 19, 20, 25, or at least 30 consecutive nucleotides of a sense or antisense strand of a plant chorismate synthase or chorismate mutase gene or RNA. Preferably, the sequence identity will be at least 70%, more preferably at least 75%, 80%, 85%, 90%, 95%, 98% and most preferably at least 99%.

In one embodiment, the invention provides an antisense molecule, wherein said molecule comprises SEQ ID NO:7, SEQ ID NO:8, SEQ ID NO:9, SEQ ID NO:10 or at least 14 consecutive nucleotides thereof.

In another embodiment, the invention provides an antisense molecule, wherein said molecule has at least 95% sequence identity with at least 20, 25, 30, 40 or 50 consecutive nucleotides of SEQ ID NO:7, SEQ ID NO:8, SEQ ID NO:9, or SEQ ID NO:10. In another embodiment, the antisense molecule has at least 80%, 85%, 90%, 95% 98% 99% or 100% sequence identity with at least 100 consecutive nucleotides of SEQ ID NO:7, SEQ ID NO:8, SEQ ID NO:9, or SEQ ID NO:10.

The polynucleotides of the invention may be specific for any one or more plant chorismate synthase of chorismate mutase genes or RNAs. The genomic sequence and/or cDNA of chorismate synthases and chorismate mutases from a variety of organisms are known. Examples include, but are not limited to those described in Braun et al. (1996) *Planta* 200:64–70 (*Lycopersicon esculentum* chorismate synthase); Charles et al. (1990) *J Gen Microbiol* 136:353–358 (*C. sempervirens* chorismate synthase); GenBank accession No:AW568644, AW279504, AW277636 and A1941440 (*Glycine max* (soybean) chorismate synthase cDNA); GenBank Accession No: A1729656 (Cotton fiber *Gossypium hirsutum* chorismate synthase cDNA); Henstrand et al. (1995) *J Biol Chem* 270:20447–20452 (*Neurospora crassa* chorismate synthase cDNA); Jones et al. (1991) *Mol Microbiol* 5:2143–2152 (*Saccharomyces cerevisiae* chorismate synthase); Schaller et al. (1991) *J Biol Chem* 266:21434–21438 (*Bacillis subtilis* chorismate synthase); Roberts et al. (1998) *Nature* 393:801–805 (*T. gondii* and *P. falciparum* chorismate synthases); Horseburgh et al. *Microbiology* 142:2943–2950 (1996) (*Staphlococcus aureus* chorismate synthase); Mobley et al. (1999) *Gene* 240:115–123 (*A. thaliana* chorismate mutase-1, 2 and 3); Lambert et al. (1999) *Mol Plant Microbe Interact* 12:328–336 (*Meloidogyne javanica* chorismate mutase); Eberhard et al. (1996) *Plant Mol Biol* 4:917–922 (tomato cytosolic chorismate mutase); Eberhard et al (1996) *Plant J* 5:815–821 (*A. thaliana* cytosolic and plastidic chorismate mutase); GenBank accession No:AW666427 (*Glycine max* chorismate mutase cDNA); GenBank Accession No:AW164012 (*Lotus japonicus* chorismate mutase cDNA); GenBank Accession No:AJ004916 (*Prunus avium* chorismate mutase mRNA); GenBank Accession No:AA751486 (Rice chorismate mutase-1 cDNA); GenBank Accession No:AF012867 (*Petroselinum crispum* (parsley) chorismate mutase mRNA); GenBank Accession No:AF012866 (*Petroselinum crispum* chorismate mutase mRNA) and Krappmann et al. (1999) *J Biol Chem* 274:22275–22282 (*Aspergillus nidulans* and *cerevisae* chorismate mutases). Additional chorismate synthase and chorismate mutase cDNAs have been reported in the literature and public databases.

An *A. thaliana* chorismate synthase partial cDNA is disclosed in SEQ ID NO:1. Chorismate mutase-1, chorismate mutase-2 and chorismate mutase-3 full length cDNAs are shown in SEQ ID NO:2, SEQ ID NO:3 and SEQ ID NO:4, respectively. The *A. thaliana* chorismate mutase-1 and chorismate mutase-2 genomic DNAs are shown in SEQ ID NO:5 and SEQ ID NO:6, respectively.

Additional plant chorismate synthase and chorismate mutase cDNAs and genes may be identified using known chorismate synthase and chorismate mutase cDNAs and genes. For example, the sequences shown in SEQ ID NOs:1–6, as well as the sequences of other known chorismate mutase and chorismate synthase genes, cDNAs and proteins can be used to identify homologous plant chorismate mutase and chorismate synthase genes and cDNAs. See, for example, *Current Protocols in Molecular Biology* Ausubel et al., Eds., Greene Publishing and Wiley-Interscience, New York, 1995.

Similarly, the newly identified sequences may be used to obtain additional plant chorismate mutase and synthase genes and cDNAs. In one method, known chorismate synthase and chorismate mutase sequences are used as probes to identify and clone corresponding genes or cDNAs from plants and plant libraries. Alternatively, synthetic oligonucleotides can be prepared that correspond to chorismate mutase or chorismate synthase genes or cDNAs and used as primers in PCR amplification to obtain whole or partial sequences. If desired, these partial sequences can then be used as probes to isolate chorismate mutase and chorismate synthase clones from plant genomic or cDNA libraries. Such partial or full-length sequences can be used to generate the chorismate synthase and chorismate antisense and sense polynucleotides, dsRNA and ribozymes of the invention. Methods for inhibiting expression in plants using antisense constructs are known in the art. See, for example, U.S. Pat. Nos. 5,107,065 and 5,254,800, the contents of which are incorporated by reference.

The active antisense molecules of the invention are single stranded RNA or DNA molecules. By active antisense molecule is meant that the antisense molecule is capable of selectively hybridizing with a plant chorismate synthase or chorismate mutase primary transcript or mRNA. However, it is understood that the term antisense molecules include double-stranded DNA molecules that encode an antisense RNA.

Preferably, the antisense polynucleotides of the invention are at least 8, 10, 12, 14, 16, 18, 20, 25, 30, 35, 40, 45, 50, 100, 200, 500, 1000 nucleotides or more. Antisense polynucleotides can be selected based on complementarity to plant chorismate synthase and chorismate mutase genes or RNAs. The complementarity may be to all or a portion of the gene or RNA. Furthermore, the complementarity need not be exact, so long as the antisense molecule is specific for at least one plant chorismate mutase or chorismate synthase RNA. In general, the degree of complementarity necessary or antisense inhibition is related to the length of the hybridizing sequences. Preferably, the complementarity is at least 90%, more preferably 95%, even more preferably at least 98% and most preferably 100%. Antisense polynucleotides may be designed to bind to exons, introns, exon-intron boundaries, the promoter and other control regions, such as the transcription and translational initiation sites. Methods for inhibiting plant gene expression using antisense RNA corresponding to entire and partial cDNA, 3' non-coding regions, as well as relatively short fragments of coding regions are known in the art. See, for example, Sheehy et al. (1988) *Proc Natl Acad Sci USA* 85:8805–8809; Cannon et al. (1990) *Plant Mol Biol* 15:39–47; and Chng et al. (1989) *Proc Natl Acad Sci USA* 86:10006–10010. Van der Krol et al. (1988) *Biotechniques* 6:958–976 describe the use of antisense RNA to inhibit plant genes in a tissue-specific manner.

As an alternative to antisense polynucleotides, ribozymes, sense polynucleotides or dsRNA may be used to reduce plant chorismate mutase or chorismate synthase gene expression. A ribozyme, or catalytic RNA can catalyze the hydrolysis of RNA phosphodiester bonds in trans, and thus can cleave other RNA molecules. Cleavage of a target RNA can decrease stability of the RNA and prevent translation of a full length protein encoded by that RNA.

Ribozymes contain a first RNA sequence that is complementary to a target RNA linked to a second enzymatic RNA sequence that catalytically cleaves the target RNA. Thus, the ribozyme first binds a target RNA through complementary base-pairing, and then acts enzymatically to cut the target RNA. Ribozymes may be designed to bind to exons, introns, exon-intron boundaries and control regions, such as the translational initiation sites.

At least six types of naturally-occurring enzymatic RNAs, including hairpin ribozymes and hammerhead ribozymes, have been described. The hairpin ribozyme can be assembled in various combinations to catalyze a unimolecular, bimolecular or a trimolecular cleavage/ligation reaction (Berzal-Herranz et al. (1992) *Genes & Develop* 6:129; Chowrira and Burke (1992) *Nucleic Acids Res* 20:2835; Komatsu et al. (1993) *Nucleic Acids Res* 21:185; Komatsu et al. (1994) *J Am Chem Soc* 116:3692). Increasing the length of helix 1 and helix 4 regions do not affect the catalytic activity of the hairpin ribozyme (Hisamatsu et al., supra; Chowrira and Burke, supra; Anderson et al. (1994) *Nucleic Acids Res* 22:1096). For a review of various ribozyme motifs, and hairpin ribozyme in particular, see Ahsen and Schroeder (1993) *Bioessays* 15:299; Cech (1992) *Curr Opi Struc Bio* 2:605; and Hampel et al. (1993) *Methods: A Companion to Methods in Enzymology* 5:37.

The invention provides ribozymes that are specific for at least one plant chorismate synthase RNA or plant chorismate mutase RNA. In one embodiment, the ribozyme is specific for an Arabidopsis chorismate synthase or chorismate mutase RNA. A ribozyme that is “specific for at least one plant chorismate synthase RNA or plant chorismate mutase RNA” will contain a polynucleotide sequence that specifically hybridizes to a target plant chorismate synthase or chorismate mutase primary transcript or mRNA (the “target”) and cleaves that target. The portion of the ribozyme that hybridizes to the transcript or RNA is typically at least 7 nucleotides in length. Preferably, this portion is at least 8, 9, 10, 12, 14, 16, 18 or 20 or more nucleotides in length. The portion of the ribozyme that hybridizes to the target need not be completely complementary to the target, as long as the hybridization is specific for the target. In preferred embodiments the ribozyme will contain a portion having at least 7 or 8 nucleotides that have 100% complementarity to a portion of the target RNA.

In one embodiment, the target RNA is an Arabidopsis chorismate synthase or chorismate mutase RNA.

Accordingly, the invention provides a ribozyme specific for an Arabidopsis chorismate synthase RNA, wherein said ribozyme comprises at least 7 consecutive nucleotides of SEQ ID NO:7. Alternatively, the invention provides a ribozyme specific for an Arabidopsis chorismate mutase RNA, wherein said ribozyme comprises at least 7 consecutive nucleotides of SEQ ID NO:8, SEQ ID NO:9 or SEQ ID NO:10.

Methods for designing and preparing ribozymes are known to those skilled in the art. See, for example, U.S. Pat. Nos. 6,025,167; 5,773,260; 5,695,992; 5,545,729; 5.496,698 and 4,987,071, the contents of which are incorporated by reference; Van Tol et al. (1991) *Virology* 180:23; Hisamatsu et al. (1993) *Nucleic Acids Symp Ser* 29:173; Berzal-Herranz et al. (1993) *EMBO J* 12:2567 (describing essential nucleotides in the hairpin ribozyme); Hampel and Tritz, (1989) *Biochemistry* 28:4929; Haseloff et al. (1988) *Nature* 334:585–591, Haseloff and Gerlach (1989) *Gene* 82:43 (describing sequences required for self-cleavage reactions); and Feldstein et al. (1989) *Gene* 82:53.

In still yet another aspect, the invention provides double-stranded RNA (dsRNA) that is specific for a plant chorismate mutase or chorismate synthase gene or RNA. The term dsRNA, as used herein, refers to RNA hybrids comprising two strands of RNA. The dsRNAs of the invention may be linear or circular in structure. The hybridizing RNAs may be substantially or completely complementary. By substantially complementary, is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs of will be of identical length with no over hanging 5' or 3' ends and no gaps. However, dsRNAs having 5' or 3' overhangs of up to 100 nucleotides may be used in the methods of the invention.

Thus, in one embodiment, the invention provides a dsRNA, comprising: a first ribonucleic acid having at least 80% sequence identity with at least 100 consecutive nucleotides of a plant chorismate synthase RNA or a plant chorismate mutase RNA; and a second ribonucleic acid that is substantially complementary to said first ribonucleic acid.

Preferably, the first ribonucleic acid of the dsRNA of the invention has at least 80% sequence identity with at least 100 consecutive nucleotides of SEQ ID NO:1, SEQ ID NO:2, SEQ ID NO:3, SEQ ID NO:4, SEQ ID NO:5 or SEQ ID NO:6. Alternatively, the first ribonucleic hybridizes to SEQ ID NO:7, SEQ ID NO:8, SEQ ID NO:9 or SEQ ID NO:10 under high stringency conditions.

The dsRNA may comprise ribonucleotides or ribonucleotide analogs, such as 2'-O-methyl ribosyl residues or combinations thereof. See U.S. Pat. Nos. 4,130,641 and 4,024,222. A dsRNA polyriboinosinic acid:polyribocytidylic acid is described in U.S. Pat. No. 4,283,393.

Methods for making and using dsRNA are known in the art. One method comprises the simultaneous transcription of two complementary DNA strands, either in vivo, or in a single in vitro reaction mixture. See, for example, U.S. Pat. No. 5,795,715, the contents of which is incorporated by reference. dsRNA can be introduced into a plant or plant cell directly by standard transformation procedures. Alternatively, dsRNA can be expressed in a plant cell by transcribing two complementary RNAs.

Other methods for the inhibition of endogenous chorismate mutase and chorismate synthase gene expression, such as triple helix formation (Moser et al. (1987) *Science* 238:645–650 and Cooney et al. (1988) *Science* 241:456–459) and cosuppression (Napoli et al. (1990) *The Plant Cell* 2:279–289) are known in the art. Partial and full-length cDNAs have been used for the cosuppression of endogenous plant genes. See, for example, U.S. Pat. Nos. 4,801,340, 5,034,323, 5,231,020 and 5,283,184, the contents of which are incorporated by reference, Van der Kroll et al. (1990) *The Plant Cell* 2:291–299, Smith et al. (1990) *Mol Gen Genetics* 224:477–481 and Napoli et al. (1990) *The Plant Cell* 2:279–289.

For sense suppression, it is believed that introduction of a sense polynucleotide blocks transcription of the corresponding target gene. The sense polynucleotide will have at least 65% sequence identity with the target plant chorismate synthase or chorismate mutase gene or RNA. Preferably, the percent identity is at least 80%, 90%, 95% or more. The introduced sense polynucleotide need not be full length relative to the target gene or transcript. Preferably, the sense polynucleotide will have at least 65% sequence identity with at least 100 consecutive nucleotides of a primary transcript or mRNA of the target endogenous plant gene. The regions of identity can comprise introns and and/or exons and untranslated regions. The introduced sense polynucleotide may be present in the plant cell transiently, or may be stably integrated into a plant chromosome or extrachromosomal replicon.

In another aspect, the invention provides a method for the identification of a candidate chorismate synthase antisense, dsRNA, sense or ribozyme molecule that inhibits a plant chorismate synthase activity, comprising:

a) contacting a plant cell expressing a chorismate synthase protein with said antisense, dsRNA, sense or ribozyme molecule; and
b) comparing the growth of said cell from step (a) with the growth of said cell in the absence of said antisense, dsRNA, sense or ribozyme molecule; wherein a decrease in growth in the presence of said antisense, dsRNA, sense or ribozyme molecule is indicative of the molecule being an inhibitor of chorismate synthase activity.

Similarly, the invention provides a method for the identification of a candidate chorismate mutase antisense, dsRNA, sense or ribozyme molecule that inhibits a plant chorismate mutase activity, comprising:

a) contacting a plant cell expressing a chorismate mutase protein with said antisense, dsRNA, sense or ribozyme molecule; and
b) comparing the growth of said cell from step (a) with the growth of said cell in the absence of said antisense, dsRNA, sense or ribozyme molecule; wherein a decrease in growth in the presence of said antisense, dsRNA, sense or ribozyme molecule is indicative of the molecule being an inhibitor of chorismate mutase activity.

Preferably, the plant cell is a cell in tissue culture. The plant cell may be contacted with the antisense, dsRNA, sense or ribozyme molecule by providing the molecule in the tissue culture medium. Alternatively, the plant cell can be contacted with the molecule by expressing it in the plant cell. Any method for measuring plant cell growth can be used. Such methods are known to those skilled in the art.

Expression of the polynucleotides of the invention in a plant, plant cell or plant tissue will result in the modulation of plant growth or development. Accordingly, the invention provides recombinant expression cassettes, comprising the antisense, sense, dsRNA or ribozyme polynucleotides of the invention, wherein said polynucleotide is operably linked to a promoter that can be active in a plant cell.

The expression cassettes of the invention contain 5' and 3' regulatory sequences necessary for transcription and termination of the polynucleotide of interest. Thus, the expression cassettes will include a promoter and a transcriptional terminator. Other functional sequences may be included in the expression cassettes of the inventions. Such functional sequences include, but are not limited to, introns, enhancers and translational initiation and termination sites and polyadenylation sites. The control sequences can be those that can function in at least one plant, plant cell or plant tissue. These sequences may be derived form one or more genes, or can be created using recombinant technology.

Promoters useful in the expression cassettes of the invention include any promoter that is capable of initiating transcription in a plant cell. Such promoters include, but are not limited to those that can be obtained from plants, plant viruses and bacteria that contain genes that are expressed in plants, such as Agrobacterium and Rhizobium.

The promoter may be constitutive, inducible, developmental stage-preferred, cell type-preferred, tissue-preferred or organ-preferred. Constitutive promoters are active under most conditions. Examples of constitutive promoters include the CaMV 19S and 35 S promoters (Odell et al. (1985) *Nature* 313:810–812), the 2× CaMV 35S promoter (Kay et al. (1987) *Science* 236:1299–1302) the Sepl promoter, the rice actin promoter (McElroy et al. (1990) *Plant Cell* 2:163–171), the Arabidopsis actin promoter, the ubiquitan promoter (Christensen et al. (1989) *Plant Molec Biol* 18:675–689); pEmu (Last et al. (1991) *Theor Appl Genet* 81:581–588), the figwort mosaic virus 35S promoter, the Smas promoter (Velten et al. (1984) *EMBO J* 3:2723–2730), the GRP1-8 promoter, the cinnamyl alcohol dehydrogenase promoter (U.S. Pat. No. 5,683,439), promoters from the T-DNA of Agrobacterium, such as mannopine synthase, nopaline synthase, and octopine synthase, the small subunit of ribulose biphosphate carboxylase (ssuRUBISCO) promoter, and the like.

Inducible promoters are active under certain environmental conditions, such as the presence or absence of a nutrient or metabolite, heat or cold, light, pathogen attack, anaerobic conditions, and the like. For example, the hsp80 promoter from Brassica is induced by heat shock, the PPDK promoter is induced by light, the PR-1 promoter from tobacco, Arabidopsis and maize are inducible by infection with a pathogen, and the Adhl promoter is induced by hypoxia and cold stress.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters and the like.

In a preferred embodiment, the promoter is a male tissue-preferred promoter. Male tissues include pollen, tapetum, anther, tassel, pollen mother cells and microspores. Ms45 is an example of a male-preferred promoter (U.S. Pat. No. 6,037,523). Other tissue preferred, developmental stage preferred and/or inducible promoters include, but are not limited to Prha (expressed in root, seedling, lateral root, shoot apex, cotyledon, petiol, inflorescence stem, flower, stigma, anthers, and silique, and auxin-inducible in roots); VSP2 (expressed in flower buds, flowers, and leaves, and wound inducible); SUC2 (expressed in vascular tissue of cotyledons, leaves and hypocotyl phloem, flower buds, sepals and ovaries); AAP2 (silique-preferred); SUC1 (Anther and pistil preferred); AAP1 (seed preferred); Saur-AC1 (auxin inducible in cotyledons, hypocotyl and flower); Enod 40 (expressed in root, stipule, cotyledon, hypocotyl and flower); amd VSP1 (expressed in young siliques, flowers and leaves).

Seed preferred promoters are preferentially expressed during seed development and/or germination. For example, seed preferred promoters can be embryo-preferred, endosperm preferred and seed coat-preferred. See Thompson et al. (1989) *BioEssays* 10:108. Examples of seed preferred promoters include, but are not limited to cellulose synthase (celA), Ciml, gamma-zein, globulin-1, maize 19 kD zein (cZ19B1) and the like.

Other promoters useful in the expression cassettes of the invention include, but are not limited to, the major chlorophyll a/b binding protein promoter, histone promoters, the prolifera promoter, the Ap3 promoter, the β-conglycin promoter, the phaseolin promoter, the napin promoter, the soy bean lectin promoter, the maize 15 kD zein promoter, the 22 kD zein promoter, the 27 kD zein promoter, the g-zein promoter, the waxy, shrunken 1, shrunken 2 and bronze promoters, the Zm 13 promoter (U.S. Pat. No. 5,086,169), the maize polygalacturonase promoters (PG) (U.S. Pat. Nos. 5,412,085 and 5,545,546) and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). Some examples of such heterologous DNA binding domains include the LexA and GAL4 DNA binding domains. The LexA DNA-binding domain is part of the repressor protein LexA from *Escherichia coli* (*E. Coli*) (Brent and Ptashne, *Cell* 43:729–736 (1985)). In one preferred embodiment, the promoter comprises a minimal promoter operably linked to an upstream activation site comprising four DNA-binding domains of the yeast transcriptional activator GAL4. Schwechheimer et al. (1998) *Plant Mol Biol* 36:195–204. The sequence of this promoter is shown in SEQ ID NO:11.

Polyadenlation signals include, but are not limited to, the Agrobacterium octopine synthase signal (Gielen et al. (1984) *EMBO J* 3:835–846) and the nopaline synthase signal (Depicker et al. (1982) *Mol and Appl Genet* 1:561–573).

Transcriptional termination regions include, but are not limited to, the terminators of the *A. tumefaciens* Ti plasmid octopine synthase and nopaline synthase genes. See Ballas et al. (1989) *Nuc Acid Res* 17:7891–7903, Guerineau et al. (1991) *Mol Gen Genet* 262:14144, Joshi et al. (1987) *Nuc Acid Res* 15:9627–9639, Mogen et al. (1990) *Plant Cell* 2:1261272, Munroe et al. (1990) *Gene* 91:15158, Proudfoot (1991) Cell 64:671–674, and Sanfacon et al. (1991) Genes Devel 5:14149. If translation of the transcript is desired, translational start and stop codons can also be provided.

The expression cassettes of the invention may be covalently liked to a polynucleotide encoding a selectable or screenable marker. Examples of such markers include genes encoding drug or herbicide resistance, such as hygromycin resistance (hygromycin phosphotransferase (HPT)), spectinomycin (encoded by the aada gene), kanamycin and gentamycin resistance (neomycin phosphotransferase (nptII)), streptomycin resistance (streptomycin phosphotransferase gene (SPT)), phosphinothricin or basta resistance (barnase (bar)), chlorsulfuron reistance (acetolactase synthase (ALS)), chloramphenicol resistance (chloramphenicol acetyl transferase (CAT)), G418 resistance, lincomycin resistance, methotrexate resistance, glyphosate resistance, and the like. Preferably, the expression cassette is linked to the bar gene. In addition, the expression cassettes of the invention may be covalently linked to genes encoding enzymes that are easily assayed, for example, luciferase, alkaline phosphatase, β-galactosidase (β-gal), β-glucuronidase (GUS) and the like.

In one embodiment, the invention provides an expression cassette, comprising a polynucleotide encoding a antisense RNA that is specific for a plant chorismate synthase RNA or plant chorismate mutase RNA, wherein said polynucleotide is operably linked to a promoter that can be active in a plant cell.

In preferred embodiments, the antisense RNA comprises SEQ ID NO:7, SEQ ID NO:8, SEQ ID NO:9 or SEQ ID NO:10. In another embodiment, the antisense RNA has at least 80% sequence identity with at least 20 consecutive nucleotides of SEQ ID NO:7, SEQ ID NO:8, SEQ ID NO:9 or SEQ ID NO:10. In still another embodiment, the antisense RNA hybridizes under high stringency conditions to the polynucleotide of SEQ ID NO:1, SEQ ID NO:2, SEQ ID NO:3, SEQ ID NO:4, SEQ ID NO:5 or SEQ ID NO:6.

In another aspect, the invention provides an expression cassette, comprising a polynucleotide encoding a plant chorismate synthase-specific ribozyme or a plant chorismate mutase-specific ribozyme, wherein said polynucleotide is operably linked to a promoter that can be active in a plant cell. Preferably, the chorismate synthase-specific ribozyme comprises at least 7, 8, 9, 10, 11, 12, 13, 14 or at least 15 consecutive nucleotides of SEQ ID NO:7, SEQ ID NO:8, SEQ ID NO:9 or SEQ ID NO:10.

In still another aspect, the invention provides an expression cassette for expressing a dsRNA, comprising: a first ribonucleic acid having at least 80% sequence identity with at least 100 consecutive nucleotides of a plant chorismate synthase RNA or a plant chorismate mutase RNA; and a second ribonucleic acid that is substantially complementary to said first ribonucleic acid, wherein each of said first and second ribonucleotides are operably linked to at least one promoter that can initiate transcription in a plant cell.

In a preferred embodiment, the first ribonucleotide has at least 80% sequence identity with at least 100 consecutive nucleotides of SEQ ID NO:1, SEQ ID NO:2, SEQ ID NO:3, SEQ ID NO:4, SEQ ID NO:5 or SEQ ID NO:6. Alternatively, the first ribonucleotide hybridizes to SEQ ID NO:7, SEQ ID NO:8, SEQ ID NO:9 or SEQ ID NO:10 under high stringency conditions.

In another aspect, the invention provides vectors containing the expression cassettes of the invention. By "vector" is intended a polynucleotide sequence that is able to replicate in a host cell. Preferably the vector contains genes that serve as markers useful in the identification and/or selection of transformed cells. Such markers include, but are not limited to barnase (bar), G418, hygromycin, kanamycin, bleomycin, gentamicin and the like. The vector can comprise DNA or RNA and can be single or double stranded, and linear or circular. Various plant expression vectors and reporter genes are described in Gruber et al. in *Methods in Plant Molecular Biology and Biotechnology*, Glick et al., eds, CRC Press, pp.89–119, 1993; and Rogers et al. (1987) *Meth Enzymol* 153:253–277. In a preferred embodiment, the vector is an *E. coli/A. tumefaciens* binary vector. Most preferably, the expression cassette is inserted between the right and left borders of a TDNA from an Agrobacterium Ti plasmid.

Introduction of the polynucleotides of the invention (including expression cassettes and vectors) into a plant, plant cell or plant tissue will result in the modulation of plant growth. Thus, in one aspect, the invention provides plants, plant cells and plant tissues transformed with at least one polynucleotide, expression cassette or vector of the invention. By transformation is meant the introduction of a polynucleotide into a target plant cell or plant tissue.

Antisense polynucleotides, dsRNA and ribozymes can be introduced directly into plant cells, in the form of RNA. Alternatively, the antisense polynucleotides, dsRNA and ribozymes of the present invention may be provided as RNA via transcription in plant cells transformed with expression constructs encoding such RNAs.

In a preferred embodiment, a plant or plant cell is transformed with a dsRNA, comprising a first strand and a second strand, wherein said first strand is a polynucleotide having at least 80% sequence identity with at least 100 consecutive nucleotides of a plant chorismate synthase RNA or a plant chorismate mutase RNA, and said second strand is substantially complementary to said first strand.

Alternatively, a plant or plant cell is transformed with an expression cassette, comprising a polynucleotide encoding a antisense RNA that is specific for a plant chorismate synthase RNA or plant chorismate mutase RNA, wherein said polynucleotide is operably linked to a promoter that can be active in a plant cell.

In yet another embodiment, a plant or plant cell is transformed with an expression cassette, comprising a polynucleotide encoding a plant chorismate synthase-specific ribozyme or a plant chorismate mutase-specific ribozyme, wherein said polynucleotide is operably linked to a promoter that can be active in a plant cell.

In still another embodiment, a plant or plant cell is transformed with an expression cassette for expressing a dsRNA, comprising: a first polynucleotide having at least 80% sequence identity with at least 100 consecutive nucleotides of a plant chorismate synthase RNA or a plant chorismate mutase RNA, and a second polynucleotide that is substantially complementary to said first polynucleotide, wherein each of said first and second polynucleotides are operably linked to at least one promoter that can initiate transcription in a plant cell.

The polynucleotides of the invention may be introduced into any plant or plant cell. By plants is meant angiospenns (monocotyledons and dicotyledons) and gymnosperms, and the cells, organs and tissues thereof. Methods for the introduction of polynucleotides into plants and for generating transgenic plants are known to those skilled in the art. See, for example, *Weissbach & Weissbach* (1988) *Methods for Plant Molecular Biology,* Academic Press, N.Y. and Grierson & Corey (1988) *Plant Molecular Biology,* $2^{nd}$ Ed., Blackie, London, Miki et al. (1993) *Procedures for Introducing foreign DNA into Plants*, CRC Press, Inc. pp.67–80. Such methods include, but are not limited to electroporation (Fromm et al. (1985) *Proc Natl Acad Sci* 82:5824 and Riggs et al. (1986) *Proc Natl Acad Sci USA* 83:5602–5606), particle bombardment (U.S. Pat. Nos. 4,945,050 and 5,204, 253, the contents of which are incorporated by reference, Klein et al. (1987) *Nature* 327:70–73, McCabe et al. (1988) *Biotechnology* 6:923–926), microinjection (Crossway (1985) *Mol Gen Genet* 202:179–185 and Crossway et al. (1986) *Biotechniques* 4:320–334), silicon carbide mediated DNA uptake (Kaeppler et al. (1990) *Plant Cell Reporter* 9:415–418), direct gene transfer (Paszkowski et al. *EMBO J* 3:2717–2722), protoplast fusion (Fraley et al. (1982) *Proc Natl Acad Sci USA* 79:1859–1863), polyethylene glycol precipitation (Paszowski et al. (1984) *EMBO J* 3:2717–2722 and Krens et al. (1982) *Nature* 296:72–74), silicon fiber delivery, agroinfection (U.S. Pat. No. 5,188,958, incorporated herein by reference, Freeman et al. (1984) *Plant Cell Physiol* 25:1353 (liposome mediated DNA uptake), Hinchee et al. (1988) *Biotechnology* 6:915–921, Horsch et al. (1984) *Science* 233:496–498, Fraley et al. (1983) *Proc Natl Acad Sci USA* 80:4803, Hemalsteen et al. (1984) *EMBO J* 3:3039–3041, Hooykass-Van Sloteren et al. (1984) *Nature* 311:763–764, Grimslcy et al. (1987) *Nature* 325:1677–1679, Gould et al. (1991) *Plant Physiol* 95:426–434, Kindle (1990) *Proc Natl Acad Sci USA* 87:1228 (vortexing method), Bechtold et al. (1995) *In Gene Transfer to Plants*, Potrykus et al. (Eds) Springer-Verlag, New York, N.Y. pp19–23 (vacuum infiltration), Schell (1987) *Science* 237:1176–1183; and *Plant Molecular Biology Manual*, Gelvin and Schilperoort, eds., Kluwer, Dordrecht, 1994).

Preferably, the polynucleotides of the invention are introduced into a plant cell by agroinfection. In this method, a DNA construct comprising a polynucleotide of the invention is inserted between the right and left T-DNA borders in an *Agrobacterium tumefaciens* vector. The virulence proteins of the *A. tumefaciens* host cell will mediate the transfer of the inserted DNA into a plant cell infected with the bacterium. As an alternative to the *A. tumefaciens*/Ti plasmid system, *Agrobacterium rhizogenes*-mediated transformation may be used. See Lichtenstein and Fuller in: Genetic Engineering, Volume 6, Ribgy (ed) Academic Press, London, 1987; Lichtenstein and Draper, in DNA Cloning, Volume 2, Glover (ed) IRI Press, Oxford, 1985.

If one or more plant gametes are transformed, transgenic seeds and plants can be produced directly. For example, a preferred method of producing transgenic Arabidopsis seeds and plants involves agroinfection of the flowers and collection of the transgenic seeds produced from the agroinfected flowers. Alternatively, transformed plant cells can be regenerated into plants by methods known to those skilled in the art. See, for example, Evans et al, *Handbook of Plant Cell Cultures*, Vol I, MacMollan Publishing Co. New York, 1983; and Vasil, *Cell Culture and Somatic Cell Genetics of Plants*, Acad Press, Orlando, Vol II, 1986.

Once a transgenic plant has been obtained, it may be used as a parent to produce progeny plants and plant lines. Conventional plant breeding methods can be used, including, but not limited to crossing and backcrossing, self-pollination and vegetative propagation. Techniques for breeding plants are known to those skilled in the art. The progeny of a transgenic plant are included with in the scope of the invention, provided that the progeny contain all or part of the transgenic construct.

The transformed plants and plant cells of the invention include the progeny of said plant or plant cell, as long as the progeny plants or plant cells still contain the antisense expression cassette. Progeny may be generated by both asexual and sexual methods. Progeny of a plant include seeds, subsequent generations of the plant and the seeds thereof.

Introduction of the polynucleotides of the invention into a plant, plant cell or plant tissue will result in the modulation of plant growth or development. In most cases, the modulation will be a decrease or cessation of growth or development of the plant cells or tissues where the polynucleotides of the invention are expressed.

The antisense, ribozymes, dsRNA and sense polynucleotides of the invention may be directly transformed into a plant cell. Alternatively, the expression cassettes or vectors of the invention may be introduced into a plant cell. Once in the cell, expression of the antisense, ribozymes, dsRNA and sense polynucleotides of the invention may be transient or stable. Stable expression requires that all or a part of the polynucleotide, expression cassette or vector is integrated into a plant chromosome or a stable extra-chromosomal replicon.

Thus, in one aspect, the invention provides a method for modulating plant growth, comprising: introducing into a plant cell at least one polynucleotide selected from the group consisting of: a chorismate synthase-specific ribozyme, a chorismate synthase-specific antisense molecule, a chorismate synthase-specific dsRNA, a chorismate synthase-specific sense molecule, a chorismate mutase-specific ribozyme, a chorismate mutase-specific antisense molecule, a chorismate mutase-specific dsRNA and a chorismate mutase-specific sense molecule.

In one embodiment, the invention provides a method for modulating the growth of a plant, plant cell or plant tissue, comprising: transforming said plant, plant cell or plant tissue with a dsRNA, comprising: a first ribonucleic acid having at least 80% sequence identity with at least 100 consecutive nucleotides of a plant chorismate synthase RNA or a plant chorismate mutase RNA; and a second ribonucleic acid that is substantially complementary to said first ribonucleic acid.

In another embodiment, the invention provides a method for modulating the growth of a plant, plant cell or plant tissue, comprising: transforming said plant, plant cell or plant tissue with an expression cassette, comprising a polynucleotide encoding a antisense RNA that is specific for a plant chorismate synthase RNA or plant chorismate mutase RNA, wherein said polynucleotide is operably linked to a promoter that can be active in a plant cell. In a preferred embodiment, the promoter comprises a minimal promoter operably linked to an upstream activation site comprising four DNA-binding domains of the yeast transcriptional activator GAL4.

In yet another embodiment, the invention provides a method for modulating the growth of a plant, plant cell or plant tissue, comprising: transforming said plant, plant cell or plant tissue with an expression cassette, comprising a polynucleotide encoding a plant chorismate synthase-specific ribozyme or a plant chorismate mutase-specific ribozyme, wherein said polynucleotide is operably linked to a promoter that can be active in a plant cell.

In still another embodiment, the invention provides a method for modulating the growth of a plant, plant cell or plant tissue, comprising: transforming said plant, plant cell or plant tissue with an expression cassette for expressing a dsRNA, comprising: a first ribonucleic acid having at least 80% sequence identity with at least 100 consecutive nucleotides of a plant chorismate synthase RNA or a plant chorismate mutase RNA; and a second ribonucleic acid that is substantially complementary to said first ribonucleic acid, wherein each of said first and second ribonucleotides are operably linked to at least one promoter that can initiate transcription in a plant cell.

Male tissue-preferred expression of any of these RNAs in one or more male tissues will result in a male sterile plant. In general, the plant progeny obtained by cross-pollination show more vigor than the progeny obtained through self-pollination.

Thus, the invention provides a method for generating a male sterile plant, comprising:

a) transforming a plant cell with an expression cassette comprising a polynucleotide selected from the group consisting of: a plant chorismate synthase-specific ribozyme, a plant chorismate synthase-specific antisense molecule, a plant chorismate synthase-specific dsRNA, a plant chorismate synthase-specific sense molecule, a plant chorismate mutase-specific ribozyme, a plant chorismate mutase-specific antisense molecule, a plant chorismate mutase-specific dsRNA and a plant chorismate mutase-specific sense molecule, wherein said polynucleotide is operably linked to a plant male tissue-preferred promoter; and b) obtaining a plant from said transformed plant cell.

In one embodiment, the male-tissue preferred promoter is a pollen-preferred promoter.

Ovule-preferred expression of the polynucleotides, expression cassettes of the invention will result in a reduction of seed size. By "reduced seed size" is meant that the seed is reduced by at least 10%. Preferably, the seed is reduced in size to 25%, 50%, 75%, 90% or is absent. The seed of any plant may be reduced in size, however preferred plants include cucumbers, tomatoes, melons, cherries, grapes, pomegranates and the like.

Thus, the invention provides a method for generating a plant with reduced seed size, comprising: a) transforming a plant cell with the expression cassette comprising a polynucleotide selected from the group consisting of: a plant chorismate synthase-specific ribozyme, a plant chorismate synthase-specific antisense molecule, a plant chorismate synthase-specific dsRNA, a plant chorismate synthase-specific sense molecule, a plant chorismate mutase-specific ribozyme, a plant chorismate mutase-specific antisense molecule, a plant chorismate mutase-1-specific dsRNA and a plant chorismate mutase-specific sense molecule, wherein said polynucleotide is operably linked to an ovule-preferred promoter; and b) obtaining a plant from said transformed plant cell.

EXPERIMENTAL

Plant Growth Conditions

Unless, otherwise indicated, all plants were grown Scotts Metro-Mix™ soil (the Scotts Comapnay) in an environmental growth room at 22° C., 65% humidity, 65% humidity and a light intensity of ~100 $\mu$-E $m^{-2}$ $s^{-1}$ supplied over 16 hour day period.

Seed Sterilization

All seeds were surface sterilized before sowing onto phytagel plates using the following protocol.

1. Place approximately 20–30 seeds into a labeled 1.5 mL conical screw cap tube. Perform all remaining steps in a sterile hood using sterile technique.
2. Fill each tube with 1 mL 70% ethanol and place on rotisserie for 5 minutes.
3. Carefully remove ethanol from each tube using a sterile plastic dropper; avoid removing any seeds.
4. Fill each tube with 1 mL of 30% Clorox and 0.5% SDS solution and place on rotisserie for 10 minutes.
5. Carefully remove bleach/SDS solution.
6. Fill each tube with 1 mL sterile dI $H_2O$; seeds should be stirred up by pipetting of water into tube. Carefully remove water. Repeat 3 to 5 times to ensure removal of Clorox/SDS solution.
7. Fill each tube with enough sterile dI $H_2O$ for seed plating (~200–400 uL). Cap tube until ready to begin seed plating.

Plate Growth Assays

Surface sterilized seeds were sown onto plate containing 40 ml half strength sterile MS medium (no sucrose) and 1% Phytagel using the following protocol:

1. Using pipette man and 200 uL tip, carefully fill tip with seeds and 0.1% agarose solution. Place 10 seeds across the top of the plate, about ¼ in down from the top edge of the plate.
2. Place plate lid ¾ of the way over the plate and allow to dry for 30 minutes or until agarose solution is dry. It is important to allow agarose solution to dry completely before sealing up plates in order to prevent contamination.
3. Using sterile micropore tape, seal the edge of the plate where the top and bottom meet.
4. Place plates stored in a vertical rack in the dark at 4° C. for three days.
5. Three days after sowing, the plates transferred into a growth chamber with a day and night temperature of 22 and 20° C., respectively, 65% humidity and a light intensity of ~100 $\mu$-E $m^{-2}$ $s^{-1}$ supplied over 16 hour day period.
6. Beginning on day 3, daily measurements are carried out to track the seedlings development until day 14. Seedlings are harvested on day 14 (or when root length reaches 6 cm) for root and rosette analysis.

Example 1

Construction of a Transgenic Plant Expressing the Driver

Figure 1:
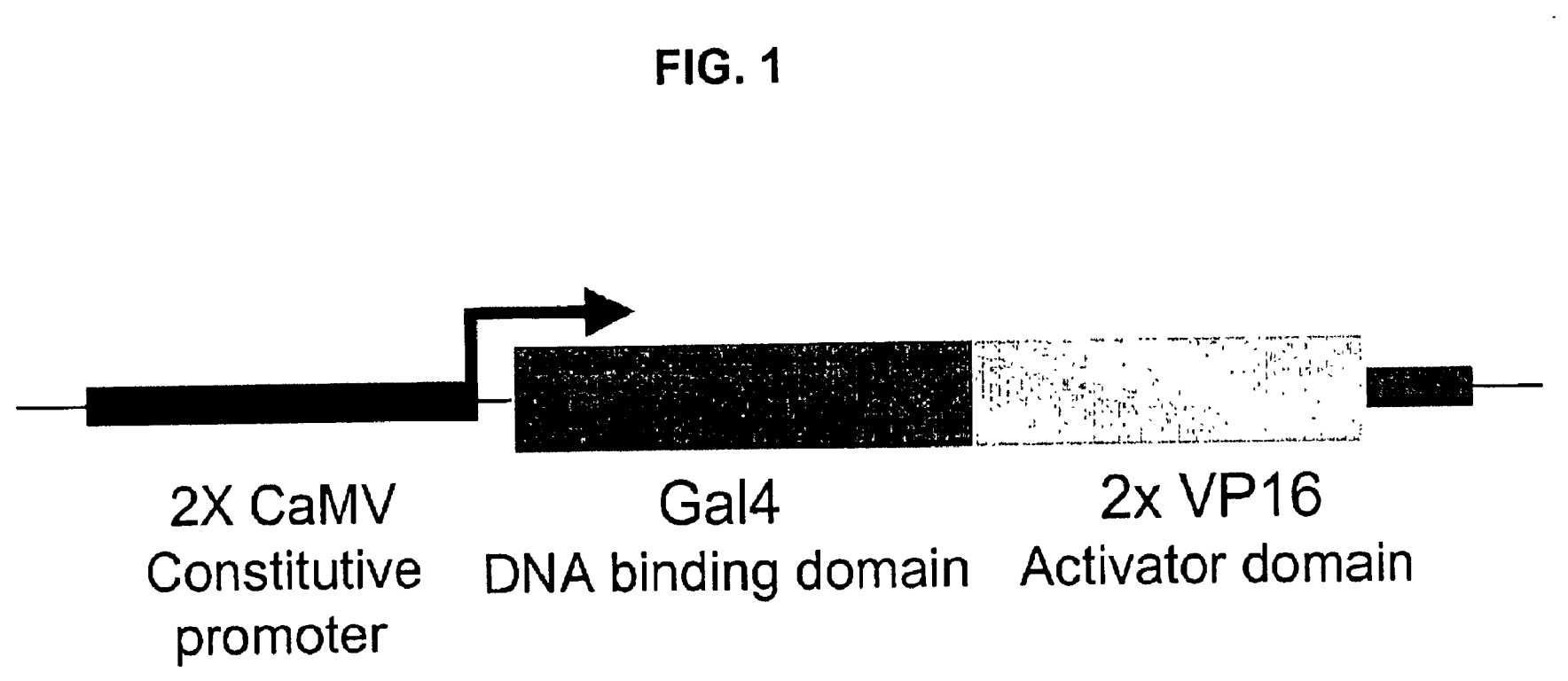

The "Driver" is an artificial transcription factor comprising a chimera of the DNA-binding domain of the yeast GAL4 protein (amino acid residues 147) fused to two tandem activation domains of herpes simplex virus protein VP16 (amino acid residues 413–490). Schwechheimer et al. (1998) *Plant Mol Biol* 36:195–204. This chimeric driver is a transcriptional activator specific for promoters having GAL4 binding sites. Expression of the driver is controlled by two tandem copies of the constitutive CaMV 35S promoter. A diagram of the driver expression cassette is shown in FIG. 1.

The driver expression cassette was introduced into *Arabidopsis thaliana* by agroinfection. Transgenic plants that stably expressed the driver transcription factor were obtained.

Example 2

Figure 3:
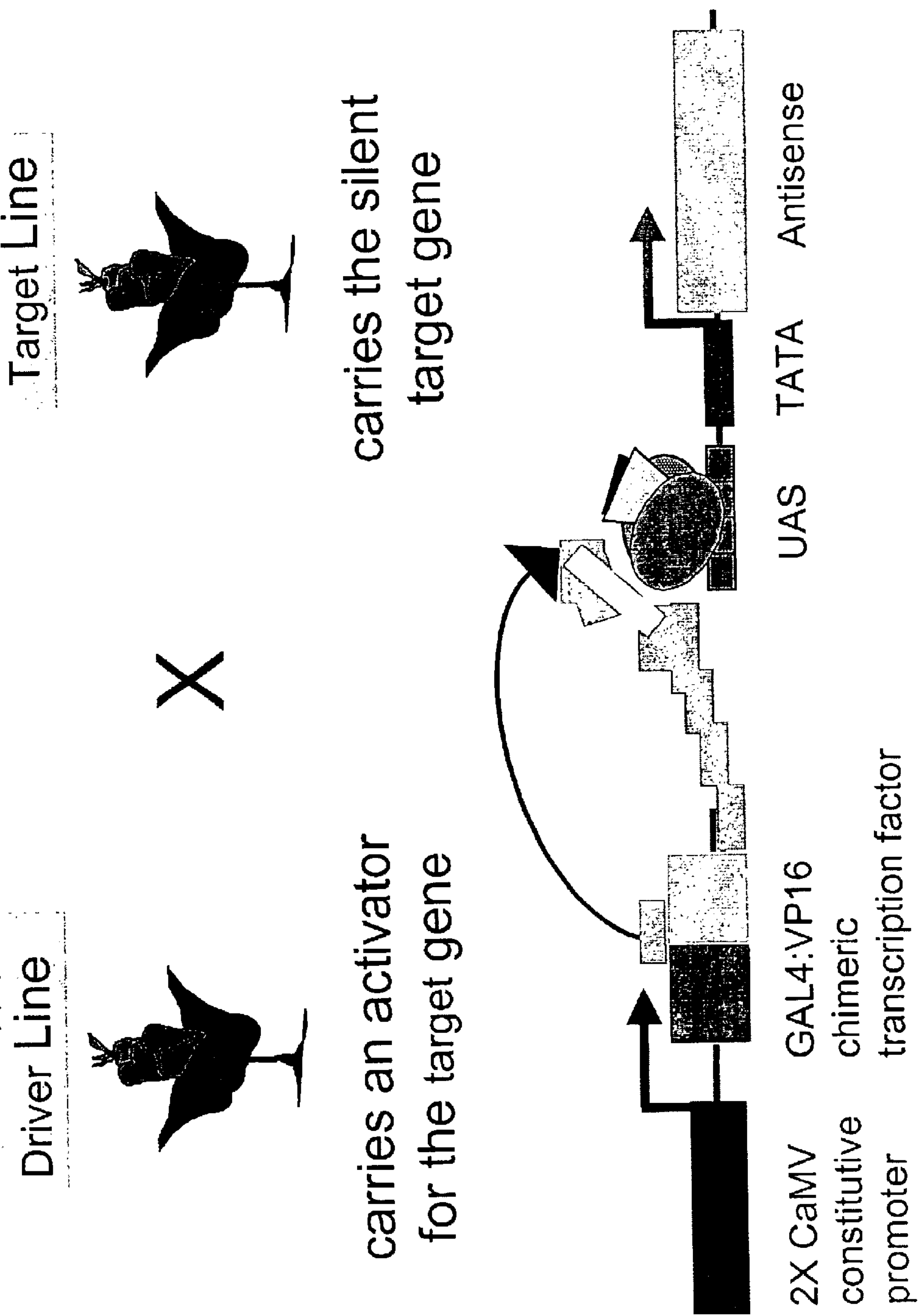
FIG. 3 shows activation of the target antisense expression cassette by the driver transactivation factor.

Construction of Chorismate Synthase and Chorismate Mutase-1 Antisense Expression Cassettes in Binary Vectors Partial cDNAs for *Arabidopsis thaliana* chorismate synthase or chorismate mutase-1 were ligated into the PacI/AscI sites of the *E. coli*/Agrobacterium binary vector PGT3.2 in the antisense orientation. This placed transcription of the chorismate mutase-1 or chorismate synthase antisense RNA under the control of an artificial promoter that is active only in the presence of the driver transcription factor described above. See FIGS. 2 and 3. The artificial promoter contains four contiguous binding sites for the GAL4 transcriptional activator upstream of a minimal promoter comprising a TATA box (SEQ ID NO:11).

The ligated DNA was transformed into *E.coli*. Kanamycin resistant clones were selected and purified. DNA was isolated from each clone and characterized by PCR and sequence analysis. pPG252 expresses chorismate synthase antisense RNA. pPG205 expresses chorismate mutase-1 antisense RNA. The antisense expression cassette and a constitutive bamase expression cassette are located between right and left T-DNA borders. Thus, this DNA can be transferred into a recipient plant cell by agroinfection.

Example 3

Transformation of Agrobacterium with Target Expression Cassettes

The binary vectors from Example 2 (pPG252 and pPG205) were transformed into *Agrobacterium tumefaciens* by electroporation. Transformed Agrobacterium colonies were isolated using Basta selection. Two resistant colonies were purified. DNA was prepared from each clone. The insert was amplified by PCR and sequenced to confirm the sequence and orientation. The clones were stored as frozen glycerol stocks.

Example 4

Construction of an Arabidopsis Chorismate Synthase and Chorismate Mutase-1 Antisense Target Plants The chorismate synthase and chorismate mutase-1 target expression cassettes were introduced into *Arabidopsis thaliana* wild type plants by the following method. Five days prior to agroinfection, the primary inflorescence of *Arabidopsis thaliana* plants grown in 2.5 inch pots were clipped in order enhance the emergence of secondary bolts.

At two days prior to agroinfection, 5 ml LB broth (10 g/L Peptone, 5 g/L Yeast extract, 5 g/L NaCl, pH 7.0 plus 25 mg/L kanamycin added prior to use) was inoculated with a clonal glycerol stock of Agrobacterium carrying pPG252, pPG205 or pPG238. The cultures were incubated overnight at 28° C. at 250 rpm until the cells reached stationary phase. The following morning, 200 ml LB in a 500 ml flask was inoculated with 500 $\mu$l of the overnight culture and the cells were grown to stationary phase by overnight incubation at 28° C. at 250 rpm. The cells were pelleted by centrifugation at 8000 rpm for 5 minutes. The supernatant was removed and excess media was removed by setting the centrifuge bottles upside down on a paper towel for several minutes. The cells were then resuspended in 500 ml infiltration medium (autoclaved 5% sucrose) and 250 $\mu$l/L Silwet L-77™ (84% polyalkyleneoxide modified heptamethyltrisiloxane and 16% allyloxypolyethyleneglycol methyl ether), and transferred to a one liter beaker.

The previously clipped Arabidopsis plants were dipped into the Agrobacterium suspension so that all above ground parts were immersed and agitated gently for 10 seconds. The dipped plants were then cover with a tall clear plastic dome in order to maintain the humidity, and returned to the growth room. The following day, the dome was removed and the plants were grown under normal light conditions until mature seeds were produced. Mature seeds were collected and stored desiccated at 4° C.

Transgenic Arabidopsis T1 seedlings were selected using glufosinate treatment. Approximately 70 mg seeds from an agrotransformed plant were mixed approximately 4:1 with sand and placed in a 2 ml screw cap cryo vial.

The surface of the seeds was sterilized using the chlorine gas method. Briefly, the open vials were placed in a vacuum desiccator in a safety hood. A glass beaker containing 200 ml 5.25% sodium hypochlorite solution was placed in the desiccator. Two ml concentrated HCl was added to the hypochlorite solution and the cover was placed on the desiccator. Vacuum was applied briefly to seal the dessicator, and the seeds were left in the desiccator overnight.

One vial of sterilized seeds was then sown in a cell of an 8 cell flat. The flat was covered with a dome, stored at 4° C. for 3 days, and then transferred to a growth room. The domes were removed when the seedlings first emerged. After the emergence of the first primary leaves, the flat was sprayed uniformly with a 1:3000 dilution of Liberty™ (AgrEvo; 11.3% glufosinate) in water, 0.005% Silwet (50 $\mu$l/L) until the leaves were completely wetted. The spraying was repeated for the following two days.

Ten days after the first spraying resistant plants were transplanted to 2.5 inch round pots containing moistened sterile potting soil. The transplants were then sprayed with herbicide and returned to the growth room. These herbicide resistant plants represent stably transformed T1 plants. Mature T1 plants are then dried and harvested for T2 seeds.

Example 5

Effect of Chorismate Synthase Antisense Expression in Arabidopsis Seedlings

Figure 4:
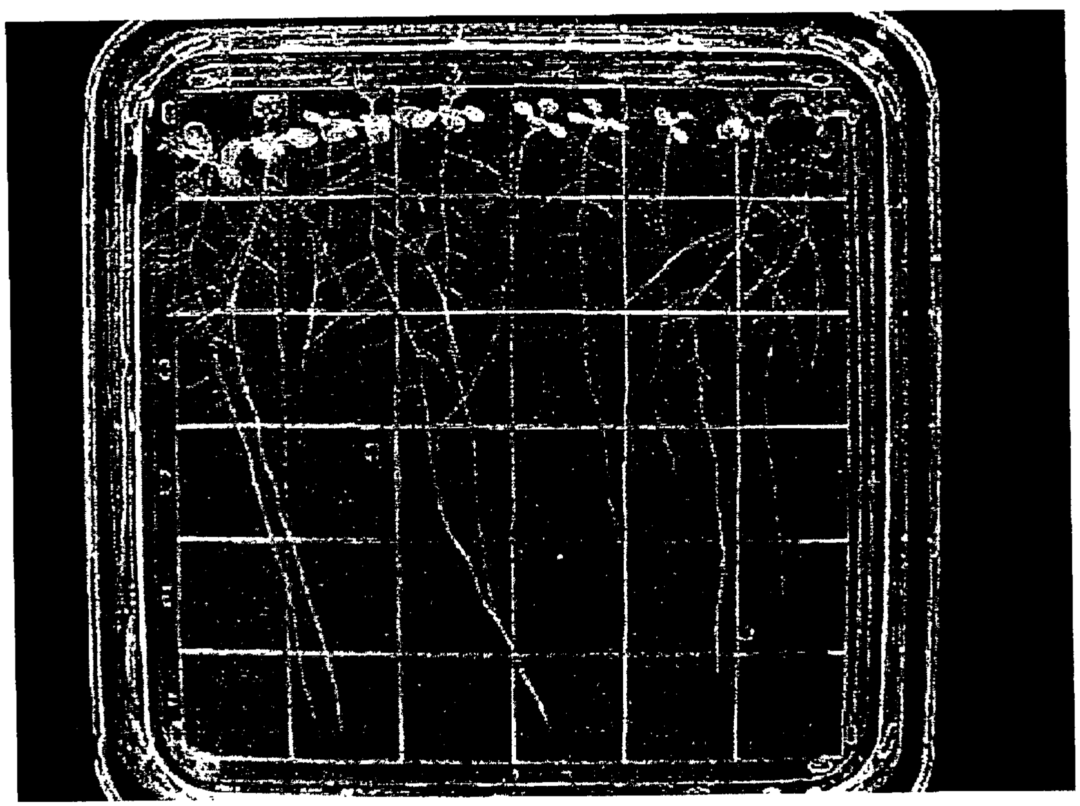
FIG. 4 is a digital image showing the effect of chorismate synthase antisense expression on *Arabidopsis thaliana* seedlings.

The chorismate synthase target plants from two transformed plant lines obtained in Example 5 were crossed with the Arabidopsis transgenic driver line described above. The resulting F1 seeds were then subjected to a PGI plate assay to observe seedling growth over a 2-week period. Seedlings were inspected daily for growth and development. During this period, a portion of seedlings derived from one of the chorismate synthase antisense target lines developed very slowly and had varying levels of developmental abnormalities. The progeny from the second line were all normal. FIG. 4 shows the effect of chorismate synthase antisense expression on Arabidopsis seedlings. The results are summarized in Table 1.

TABLE 1

Phenotypes of plants expressing chorismate synthase antisense constructs

| Construct | No. Wild Type | No. Abnormal | $\chi^2$ Value[a] | Probability[a] |
|---|---|---|---|---|
| PPG252 | 5 | 5 | 0.00 | 1.000 |

[a]Chi-square and P values (0.05) were obtained to evaluate the hypothesis that chlorosis and wild-type phenotypes are segregating in a 1:1 ratio.

The identification of one line expressing an antisense chorismate synthase RNA that produces progeny that segregate 1:1 for abnormal phenotypes when crossed with a driver line demonstrates that the chorismate synthase gene is essential for normal plant growth and development. The fact that the progeny derived from the other line did not exhibit any abnormal phenotypes is not unexpected, since it is well known that antisense expression does not work equally well in all independently transformed lines containing the same construct. For example, the failure of these lines to produce abnormal progeny when crossed with the driver plant could be due to positional silencing of antisense expression.

Example 6

Effect of Chorismate Mutase-1 Antisense Expression in Arabidopsis Seedlings

Figure 5:
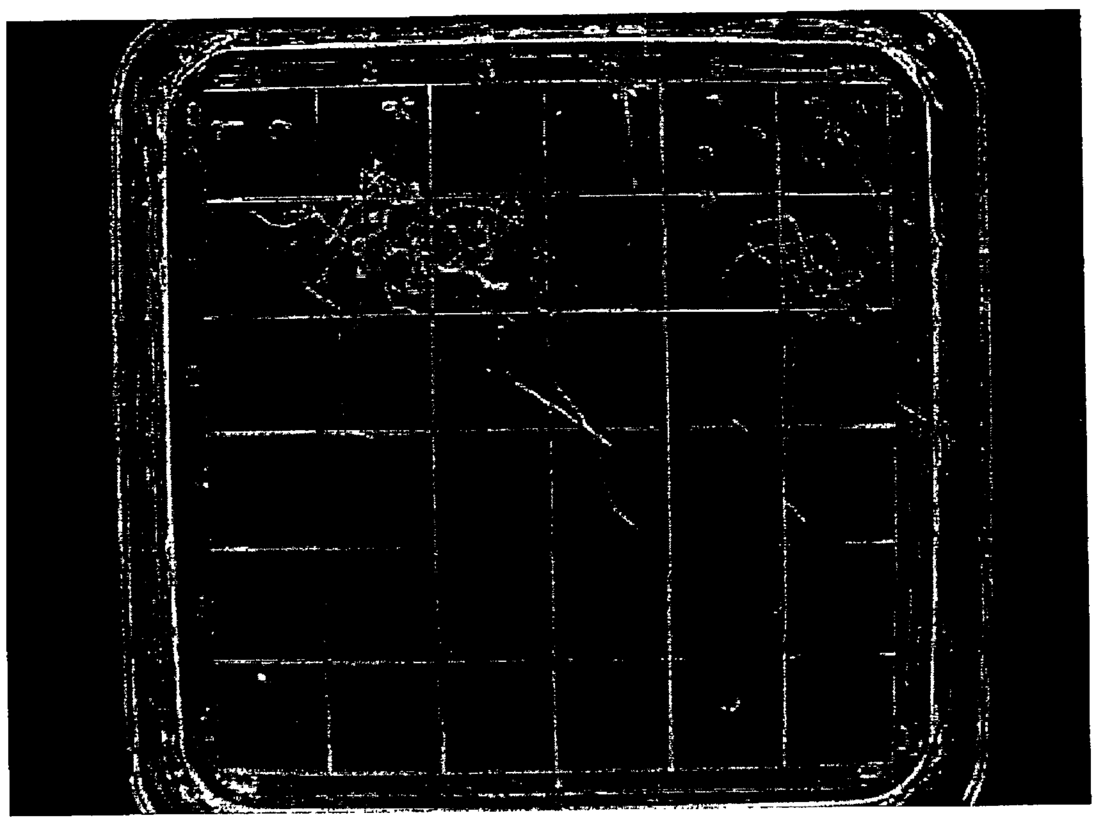
FIG. 5 is a digital photograph image showing the effect of chorismate mutase-1 antisense expression on *A. thaliana* seedlings.

The chorismate mutase-1 target plants from five transformed plant lines obtained in Example 5 were crossed with the Arabidopsis transgenic driver line described above. The resulting F1 seeds were then subjected to a PGI plate assay to observe seedling growth over a 2-week period. Seedlings were inspected daily for growth and development. FIG. 5 shows the effect of chorismate mutase antisense expression on Arabidopsis seedlings. A portion of seedlings derived from one of the chorismate synthase antisense target lines developed very slowly and had varying levels of developmental abnormalities. The results are summarized in Table 2.

TABLE 2

| Phenotypes of plants expressing chorismate mutase-1 antisense constructs | | | | |
|---|---|---|---|---|
| Line | No. Wild Type | No. Abnormal | $\chi^2$ Value[a] | Probability[a] |
| pPG205 (line 1) | 4 | 5 | 0.11 | 0.74 |
| pPG205 (line 2) | 5 | 4 | 0.11 | 0.74 |
| pPG205 (line 3) | 3 | 6 | 1.0 | 0.32 |

[a]Chi-square and P values (0.05) were obtained to evaluate the hypothesis that chlorosis and wild-type phenotypes are segregating in a 1:1 ratio.

The clear 1:1 segregation ratio observed in three out of five independent CM1 antisense lines demonstrates that the antisense expression of a chorismate mutase-1 gene results in significantly impaired growth. Thus, chorismate mutase-1 represents and essential gene for normal plant growth and development. In addition, these results show that both cDNA clones and genomic DNA can be used for antisense constructs.

Example 7

In vitro Assays for Modulators of Chorismate Synthase Activity

Chorismate synthase activity is determined according to the assay of Macheroux et al. (1996) *J Biol Chem* 271:25850–25858. Briefly, chorismate synthase activity is measured spectrophotometricly in a quartz cuvette containing 1 ml 5–10 μM reduced flavin, 90 μM EPSP, 1 mM potassium oxalate, 50 mM MOPS buffer, 10% glycerol, pH 7.5, in the presence or absence of a compound to be tested for the ability to modulate chorismate synthase activity. 5 μl of 23 μM chorismate synthase is added, and the change in absorbance at 275 nm ($\Delta\epsilon$=2630 $M^{-1}$ $cm^{-1}$), 25° C. was measured as a baseline. The absorbance is compared in the presence and absence of the test compound.

While the foregoing describes certain embodiments of the invention, it will be understood by those skilled in the art that variations and modifications may be made and still fall within the scope of the invention.

What is claimed is:

1. A method for identifying a compound as a candidate for a herbicide, comprising:

a) combining chorismate and a plant chorismate mutase under reaction conditions suitable for chorismate mutase activity;

b) combining chorismate, the plant chorismate mutase and a test compound under the reaction conditions of step (a);

c) detecting the amount of chorismate and/or prephenate in steps (a) and (b), wherein a difference in the amount detected between steps (a) and (b) indicates the test compound as a candidate for a herbicide.

2. The method of claim 1 wherein the plant chorismate mutase is from a dicotyledonous plant.

3. The method of claim 1, wherein the plant chorismate mutase is from a monocotyledonous plant.

4. The method of claim 1, wherein the plant chorismate mutase is cytosolic.

5. The method of claim 1, wherein the plant chorismate mutase is plastidic.

* * * * *